United States Patent
Pendelton et al.

(10) Patent No.: US 11,648,951 B2
(45) Date of Patent: May 16, 2023

(54) SYSTEMS AND METHODS FOR CONTROLLING ACTUATORS BASED ON LOAD CHARACTERISTICS AND PASSENGER COMFORT

(71) Applicant: Motional AD LLC, Boston, MA (US)

(72) Inventors: Scott D. Pendelton, Singapore (SG); Maurilio Di Cicco, Singapore (SG)

(73) Assignee: Motional AD LLC, Boston, MA (US)

(*) Notice: Subject to any disclaimer, the term of this patent is extended or adjusted under 35 U.S.C. 154(b) by 562 days.

(21) Appl. No.: 16/656,655

(22) Filed: Oct. 18, 2019

(65) Prior Publication Data

US 2020/0130703 A1 Apr. 30, 2020

Related U.S. Application Data

(60) Provisional application No. 62/806,403, filed on Feb. 15, 2019, provisional application No. 62/752,277, filed on Oct. 29, 2018.

(51) Int. Cl.
*B60W 50/00* (2006.01)
*B60N 2/00* (2006.01)
(Continued)

(52) U.S. Cl.
CPC ....... *B60W 50/0098* (2013.01); *A61B 5/0077* (2013.01); *A61B 5/01* (2013.01);
(Continued)

(58) Field of Classification Search
CPC ............. B60W 50/0098; B60W 40/08; B60W 2040/0872; B60W 2050/0083; B60W 2540/22; B60W 2555/20; B60W 30/182; B60W 2540/043; B60W 2540/221; B60W 2556/10; B60W 2556/50; B60W 2720/10; B60W 2720/106; B60W 2720/125; B60W 2754/20; B60W 2754/30; B60W 40/09; B60W 50/085; B60W 40/13;
(Continued)

(56) References Cited

U.S. PATENT DOCUMENTS 7,124,027 B1 10/2006 Ernest et al.
7,661,891 B2 2/2010 Heibel
(Continued)

FOREIGN PATENT DOCUMENTS

CN 104321620 1/2015
CN 105459930 4/2016
(Continued)

OTHER PUBLICATIONS

EP Search Report in European Appln. No. 19205963, dated Mar. 18, 2020, 10 pages.
(Continued)

*Primary Examiner* — Yuen Wong
(74) *Attorney, Agent, or Firm* — Fish & Richardson P.C.

(57) ABSTRACT

Among other things, we describe techniques for operation of a vehicle based on measured load characteristics and/or passenger comfort. One or more sensors of the vehicle can measure passenger data and/or load data of the vehicle. The passenger data and/or load data of the vehicle can be used by the vehicle to determine how to navigate within the surrounding environment.

20 Claims, 18 Drawing Sheets

(51) Int. Cl.
*B60W 40/08* (2012.01)
*A61B 5/0205* (2006.01)
*A61B 5/01* (2006.01)
*A61B 5/00* (2006.01)
*G06Q 30/0207* (2023.01)
*G05D 1/00* (2006.01)
*G06V 40/18* (2022.01)
*G06V 40/16* (2022.01)
*A61B 5/022* (2006.01)
*A61B 5/024* (2006.01)
*A61B 5/0533* (2021.01)

(52) U.S. Cl.
CPC ........ *A61B 5/02055* (2013.01); *A61B 5/6893* (2013.01); *B60N 2/002* (2013.01); *B60W 40/08* (2013.01); *G05D 1/0088* (2013.01); *G06Q 30/0236* (2013.01); *G06V 40/174* (2022.01); *G06V 40/18* (2022.01); *A61B 5/024* (2013.01); *A61B 5/02233* (2013.01); *A61B 5/0533* (2013.01); *B60W 2040/0872* (2013.01); *B60W 2050/0083* (2013.01); *B60W 2540/22* (2013.01); *B60W 2555/20* (2020.02); *G05D 2201/0213* (2013.01)

(58) Field of Classification Search
CPC ......... B60W 2040/1307; A61B 5/0077; A61B 5/01; A61B 5/02055; A61B 5/6893; A61B 5/02233; A61B 5/024; A61B 5/0533; A61B 5/165; A61B 5/18; B60N 2/002; G05D 1/0088; G05D 2201/0213; G06Q 30/0236; G06V 40/174; G06V 40/18; G06V 20/59; G06V 40/15; B60R 16/037
See application file for complete search history.

(56) References Cited

U.S. PATENT DOCUMENTS

| | | | |
|---|---|---|---|
| 9,971,348 | B1 | 5/2018 | Canavor et al. |
| 10,007,269 | B1 | 6/2018 | Gray |
| 10,053,088 | B1 | 8/2018 | Askeland |
| 2005/0256711 | A1 | 11/2005 | Lahti |
| 2008/0040004 | A1 | 2/2008 | Breed |
| 2008/0061988 | A1* | 3/2008 | Mock .................... H04H 20/62 701/1 |
| 2009/0074249 | A1 | 3/2009 | Moed et al. |
| 2010/0026723 | A1 | 2/2010 | Nishihara et al. |
| 2010/0114437 | A1 | 5/2010 | Boss et al. |
| 2014/0200737 | A1 | 7/2014 | Lortz et al. |
| 2014/0200863 | A1 | 7/2014 | Kamat et al. |
| 2014/0280319 | A1 | 9/2014 | Rishe |
| 2015/0363986 | A1 | 12/2015 | Hoyos et al. |
| 2016/0264131 | A1 | 9/2016 | Chan et al. |
| 2016/0350609 | A1 | 12/2016 | Mason et al. |
| 2017/0057507 | A1 | 3/2017 | Gordon et al. |
| 2017/0217445 | A1 | 8/2017 | Tzirkel-Hancock et al. |
| 2017/0267256 | A1* | 9/2017 | Minster ................ G05D 1/0088 |
| 2017/0282970 | A1 | 10/2017 | Yanez |
| 2017/0349027 | A1 | 12/2017 | Goldman-Shenhar et al. |
| 2017/0370732 | A1 | 12/2017 | Bender et al. |
| 2018/0022361 | A1 | 1/2018 | Rao et al. |
| 2018/0086344 | A1 | 3/2018 | Zhu et al. |
| 2018/0217717 | A1 | 8/2018 | Yasuda et al. |
| 2018/0267557 | A1 | 9/2018 | Yan |
| 2018/0286242 | A1 | 10/2018 | Talamonti et al. |
| 2018/0297586 | A1 | 10/2018 | Kim et al. |
| 2019/0196464 | A1 | 6/2019 | Lockwood et al. |
| 2020/0219197 | A1* | 7/2020 | Fields .................. B60W 50/12 |
| 2020/0338983 | A1 | 10/2020 | Alalao et al. |

FOREIGN PATENT DOCUMENTS

| | | |
|---|---|---|
| CN | 106068097 | 11/2016 |
| CN | 107949514 | 4/2018 |
| DE | 102013213039 | 1/2013 |
| DE | 102011116718 | 4/2013 |
| DE | 102014212898 | 1/2016 |
| DE | 102017105903 | 9/2017 |
| EP | 2511149 | 10/2012 |
| JP | 2017033542 | 2/2017 |
| WO | WO 2015134376 | 9/2015 |
| WO | WO 2018170883 | 9/2018 |

OTHER PUBLICATIONS

Hasenjager et al., "Personalization in advanced driver assistance systems and autonomous vehicles: A review," 2017 IEEE 20th International Conference on Intelligent Transportation Systems (ITSC), Oct. 16, 2017, 7 pages.

[No Author Listed], "SAE International Standard J3016: Taxonomy and Definitions for Terms Related to Driving Automation Systems for On-Road Moto Vehicles," SAE International, dated Sep. 2016, 30 pages.

DK 1rst Technical Examination in Denmark Appln. No. PA 201970133, dated Apr. 26, 2019, 10 pages.

DK 2nd Technical Examination in Denmark Appln. No. PA 201970133, dated Nov. 21, 2019, 6 pages.

DK 3rd Technical Examination in Denmark Appln. No. PA 201970133, dated Jun. 30, 2020, 7 pages.

U.S. Appl. No. 16/855,954, filed Aug. 22, 2020, Alalao.

[No Author Listed] [online], "Waze App Review," retrieved from the internet <https://www.youtube.conn/watch?v=PCO1R0oXLW8> Dec. 28, 2014, 1 pages [Video Submission].

* cited by examiner

SYSTEMS AND METHODS FOR CONTROLLING ACTUATORS BASED ON LOAD CHARACTERISTICS AND PASSENGER COMFORT

CROSS-REFERENCE TO RELATED APPLICATIONS

This application claims the benefit of U.S. Provisional Application 62/752,277, filed on Oct. 29, 2018, and U.S. Provisional Application 62/806,403, filed on Feb. 15, 2019, both of which are incorporated herein by reference in their entirety.

FIELD OF THE INVENTION

This description generally relates to the operation of a vehicle and more specifically to controlling the actuators of a vehicle based on load characteristics and passenger comfort.

BACKGROUND

Autonomous vehicles have the potential to transform transportation systems by reducing road fatalities, traffic congestion, parking congestion, and fuel efficiency. Autonomous vehicles can be designed to increase passenger comfort. Conventional methods for increasing passenger comfort may typically be based on ergonomic factors such as seat vibrations, harshness, and engine noise. Other conventional methods may be based on temperature and air quality measurement. Furthermore, some autonomous vehicles control techniques may involve using feedback algorithms to determine how much to affect control mechanisms. These feedback algorithms may generally be reactive in design.

SUMMARY

In at least one aspect of the present disclosure, a method is provided. The method includes determining, using one or more processors of a vehicle, a vehicle operation profile for the vehicle. The method includes measuring, using one or more passenger sensors of the vehicle, passenger data of at least one passenger located within the vehicle. The method includes updating, using the one or more processors, the vehicle operation profile based on the passenger data. The method includes navigating, using a control module of the vehicle, the vehicle using the updated vehicle operation profile.

Determining the vehicle operation profile can include aggregating a plurality of stored passenger profiles, wherein the plurality of stored passenger profiles is demographically similar to a stored passenger profile of the at least one passenger. The vehicle operation profile can be partially determined based on data received from a stored passenger profile of the at least one passenger. The stored passenger profile of the at least one passenger can include biometric data of the at least one passenger recorded on previous vehicle rides. The stored passenger profile of the at least one passenger can include demographic data of the at least one passenger recorded on previous vehicle rides or obtained from the at least one passenger. The stored passenger profile of the at least one passenger can include personal preference data of the at least one passenger recorded on previous vehicle rides or obtained from the at least one passenger. The vehicle operation profile can include at least one of a maximum speed limit, a maximum longitudinal acceleration limit, a maximum amplitude of fluctuation of acceleration, a maximum lateral acceleration, a maximum change in steering angle, a maximum rate of turn, or a maximum limit on a magnitude of jerk for the vehicle.

The one or more passenger sensors can include one or more biometric sensors and the passenger data comprises at least one of a skin conductance, a pulse, a heart-rate, or a body temperature. The one or more passenger sensors can include one or more imaging sensors and the passenger data comprises at least one of facial expressions or a magnitude of pupil dilation. The one or more passenger sensors can include one or more pressure sensors and the passenger data comprises a pressure exerted by the at least one passenger on seat arm rests. The one or more passenger sensors can include at least one of a heart rate monitor, a sphygmomanometer, a pupilometer, an infrared thermometer, or a galvanic skin response sensor. The one or more passenger sensors can include at least one of a heart rate monitor, a sphygmomanometer, a pupilometer, an infrared thermometer, or a galvanic skin response sensor.

The passenger data can include biometric data of the at least one passenger. The passenger data can be associated with at least one of a time of day, a geographical location, a pattern of traffic, or a weather pattern. The passenger data can be measured relative to an operating speed of the vehicle. The measuring of the passenger data can include transmitting, to a chatbot in the vehicle, data describing the vehicle operation profile to the at least one passenger, and receiving, using the chatbot, the passenger data from the at least one passenger.

The vehicle operation profile can include at least one of a lateral clearance of the vehicle from an object or a pedestrian located in an environment containing the vehicle. The vehicle operation profile can determined based on data received, using an input device of the vehicle, from the at least one passenger.

The method can further include adjusting a trajectory of the vehicle based on at least one of the passenger data or data received from a stored passenger profile of the at least one passenger. The method can further include transmitting, using a display of the vehicle, data representing ride pricing incentives to the at least one passenger to incentivize the at least one passenger to allow biometric data collection within the vehicle.

The updating of the vehicle operation profile can include receiving, using an input device of the vehicle, data from the at least one passenger, describing a drive aggressiveness metric, and adjusting the vehicle operation profile based on the drive aggressiveness metric. The updating of the vehicle operation profile can include determining an aggregate passenger comfort metric based on passenger data of a plurality of passengers in the vehicle, and adjusting the vehicle operation profile based on the aggregate passenger comfort metric. The updating of the vehicle operation profile can include determining a drive aggressiveness metric based on aggregated passenger data of a plurality of passengers in the vehicle, and adjusting the vehicle operation profile based on the drive aggressiveness metric. The updating of the vehicle operation profile can be based on a weighted aggregate of passenger comfort data of a plurality of passengers in the vehicle, and wherein passenger comfort data of a higher-priority passenger is weighted higher than passenger comfort data of a lower-priority passenger.

The method can further include associating each stored vehicle operation profile of a plurality of stored vehicle operation profiles with a level of passenger comfort based on the passenger data, and deleting a stored vehicle operation profile associated with a level of passenger comfort below a threshold.

The navigating of the vehicle can include issuing, using the control module, one or more of throttle, braking, and steering commands in accordance with the updated vehicle performance profile.

In another aspect of the present disclosure, a vehicle is provided. The vehicle includes one or more passenger sensors configured to measure passenger data of at least one passenger in the vehicle and a planning module. The planning module is configured to determine a vehicle operation profile for the vehicle, and update the vehicle operation profile based on the passenger data. The vehicle can also include a control module configured to navigate the vehicle using the updated vehicle operation profile.

In at least one other aspect of the present disclosure, a vehicle is provided. The vehicle includes one or more control systems and one or more processors configured to be communicatively coupled to the one or more control systems. The vehicle includes one or more sensors configured to be communicatively coupled to the one or more processors. The one or more sensors are configured to detect one or more load characteristics of the vehicle and transmit load data representing the one or more load characteristics to the one or more processors. The one or more processors are configured to cause the one or more control systems to modify a value of a control attribute of the vehicle in accordance with the load data.

The one or more load characteristics may comprise a weight of at least one passenger of the vehicle. The one or more load characteristics may comprise a weight of a cargo load of the vehicle. The vehicle may comprise a tow system configured to haul a cargo attachment and the one or more load characteristics may comprise the weight of the hauled cargo attachment. The one or more load characteristics may comprise a characteristic specifying one or more passenger seating locations. The one or more load characteristics may comprise a characteristic specifying seatbelt usage information of one or more passengers. The one or more load characteristics may comprise a characteristic specifying one or more passenger features. The one or more load characteristics may comprise a characteristic specifying one or more object shapes.

The one or more processors may be configured to determine the center of mass of the vehicle based on the load data and cause the one or more control systems to modify the value of the control attribute of the vehicle in accordance with the center of mass of the vehicle.

The one or more sensors may comprise a load sensor. The load sensor may be located underneath a passenger seat of the vehicle. The load sensor may be located on an axle of the vehicle. The one or more sensors may comprise a capacitive sensor. The one or more sensors may comprise an inductive sensor. The vehicle may comprise a suspension system and the one or more sensors may comprise a sensor configured to measure a compression amount of one or more springs of the suspension system. The vehicle may comprise a tow system and the one or more sensors may comprise a force sensor configured to measure at least one force applied to the tow system.

The one or more processors may be configured to receive passenger information from at least one electronic device. The received passenger information may comprise an age of one or more passengers. The received passenger information may comprise health information corresponding to one or more passengers. The received passenger information may comprise driving preference information of one or more passengers. The received passenger information may comprise load data. The load data may comprise an estimate of one or more passenger's weight. The load data may comprise an estimate of one or more passenger's cargo's weight. The load data may comprise an estimate of one or more passenger's cargo's dimension.

The one or more processors may be configured to assign a weighting value to each of the one or more load characteristics. The one or more processors may be configured to cause the one or more control systems to modify a value of a control attribute of the vehicle based at least partially on the assigned weighting values. The one or more processors are further configured to update one or more planning modules based at least partially on the load data. The one or more planning modules may include a speed profile planner, a route planner, and/or a steering profile planner. Updating the one or more planning modules may comprise selecting at least a portion of a road for the vehicle to avoid.

The control attribute may correspond to at least one of a throttle and a heading. The control attribute may correspond to at least one of a suspension level and a suspension stiffness. The control attribute may correspond to an applied torque of at least one wheel of the vehicle.

In one more aspect of the present disclosure, a method is provided. The method includes detecting, by one or more sensors, one or more load characteristics of a vehicle. The method includes transmitting, by the one or more sensors and to one or more processors communicatively coupled to the one or more sensors, load data representing the one or more load characteristics. The method includes causing, by the one or more processors, one or more control systems that are communicatively coupled to the one or more processors to modify a value of a control attribute of the vehicle in accordance with the load data.

In another aspect of the present disclosure, an autonomous vehicle is provided. The autonomous vehicle includes one or more computer processors and one or more non-transitory storage media storing instructions which, when executed by the one or more computer processors, cause performance of one or more of the previously described methods.

In another aspect of the present disclosure one or more non-transitory storage media storing instructions is provided which, when executed by one or more computing devices, cause performance of one or more of the previously described methods.

In another aspect of the present disclosure a method that includes performing a machine-executed operation involving instructions which, when executed by one or more computing devices, cause performance of one or more of the previously described methods is provided. The machine-executed operation is at least one of sending said instructions, receiving said instructions, storing said instructions, or executing said instructions.

These and other aspects, features, and implementations can be expressed as methods, apparatus, systems, components, program products, means or steps for performing a function, and in other ways.

These and other aspects, features, and implementations will become apparent from the following descriptions, including the claims.

DETAILED DESCRIPTION

Figure 1:
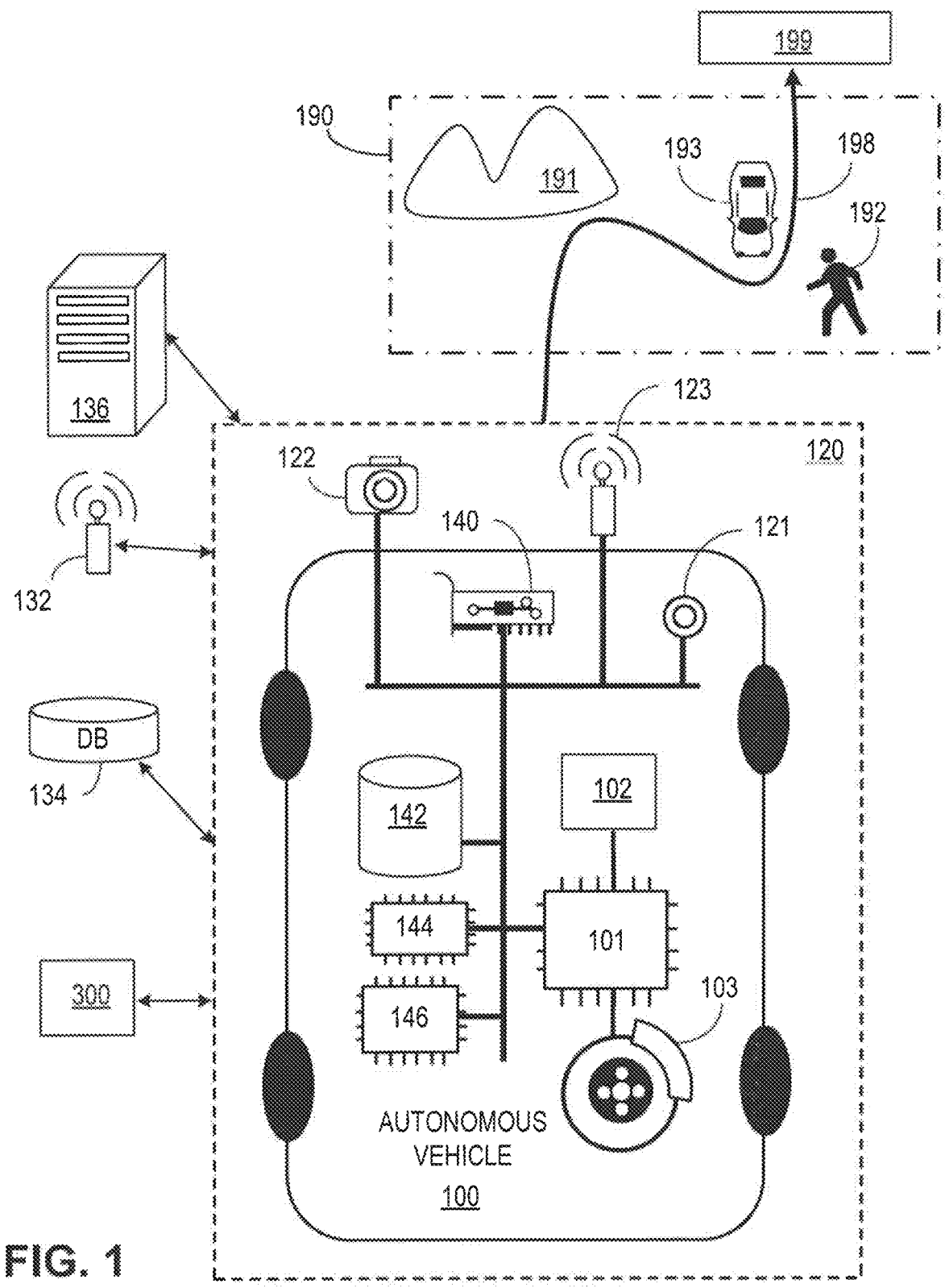
FIG. 1 illustrates an example of an autonomous vehicle (AV) having autonomous capability, in accordance with one or more embodiments.

In the following description, for the purposes of explanation, numerous specific details are set forth in order to provide a thorough understanding of the present invention. It will be apparent, however, that the present invention may be practiced without these specific details.

In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings are provided, data related to a particular heading, but not found in the section having that heading, may also be found elsewhere in this description. Embodiments are described herein according to the following outline:

1. General Overview
   2. System Overview
   3. Autonomous Vehicle Architecture
   4. Autonomous Vehicle Inputs
   5. Autonomous Vehicle Planning
   6. Autonomous Vehicle Control
   7. Architecture for Measuring and Increasing Passenger Comfort
   8. Example of Measuring and Increasing Passenger Comfort
   9. Process for Measuring and Increasing Passenger Comfort
   10. Controlling Actuators Based on Load Characteristics General Overview An autonomous vehicle (AV) may be used to automatically sense and navigate an environment within which the AV is located using a variety of techniques to perceive the AV's surroundings, including radar, laser light, GNSS (Global Navigation Satellite System), odometry, and computer vision. The potential benefits of AVs include reduced mobility and infrastructure costs, increased safety, reduction in traffic collisions, and related costs. However, conventional methods for vehicular design are insufficient for improving levels of passenger comfort in AVs. Such conventional methods are typically based on ergonomic factors such as seat vibrations, harshness, and engine noise. Conventional methods, based on temperature and air quality measurement, are similarly inadequate to address the design of AVs to increase passenger comfort. Therefore, there is a need for a new approach for increasing passenger comfort in autonomous vehicles. Furthermore, conventional methods of controlling actuators may generally rely on control feedback modules. These control feedback modules may be reactionary in design. However, a more proactive approach to controlling actuators may be desirable due to efficiency and safety concerns.

In an embodiment, an objective measure for deeming passenger comfort based on passenger data is disclosed. In an embodiment, the passenger data is a passenger profile that the passenger voluntarily creates when signing up for a user account on a ride-hailing application. The passenger data also includes biometric data that is recorded on previous AV rides. For example, an AV includes specialized sensors to record data such as a time of day, a location, a traffic pattern, the weather, facial expressions of the passenger, skin conductance, pulse and heart-rate, a temperature of the passenger's body, pupil dilation, and pressure on the AV seat arm rests. Each type of data can be recorded using a different sensor or a combination of different sensors, for example, heart rate monitors, a sphygmomanometer, a pupilometer, an Infrared thermometer, or a galvanic skin response sensor.

In an embodiment, other measurements for determining passenger comfort include properties detected while riding inside the AV without any visual perception of the outside world (eyes-closed metrics). For example, passengers are attenuated to detect lower amplitude fluctuations, fluctuating acceleration, longitudinal and lateral acceleration, and jerk even when they are unable to visually perceive the motion of the AV. In an embodiment, passenger comfort measurements also include eyes-open metrics such as clearance and distance from pedestrians. In an embodiment, combinations of eyes-closed and eyes-open measurements are used to define meta-measurements for passenger comfort. In one example, fluctuating acceleration, clearance, distance from pedestrians and data from pupilometers are used to create a drive aggressiveness metric.

In an embodiment, the collected passenger data is used to affect the operation of the AV. For example, a passenger may prefer that the AV always operates at a speed that is significantly lower than the legal speed limit. The AV may receive the passenger preference information explicitly from the passenger or the AV may determine this information based on an elevated heart rate and skin conductance level as detected by the passenger sensors in response to the AV operating at the legal speed limit.

In an embodiment, based on the data collected for other users, the AV builds a predictive profile for a new passenger. The AV tunes the performance of the AV based on the predictive profile of the new passenger. For example, if the new passenger is older and data collected previously from older passengers indicates that such passengers prefer leisurely, scenic routes to their destinations instead of using a shortest route, the AV may plan a leisurely, scenic route. In an embodiment, the AV incentivizes passengers to allow biometric data collection by offering users discounts on certain rides where the passengers acquiesce to having their biometric data recorded by the AV.

In one embodiment, the AV incorporates certain subsystems to enable passengers to choose from among different models of passenger comfort. For example, the AV may have a graphical user interface (GUI) accessible from inside the AV that allows passengers to adjust AV aggressiveness on the road. In embodiments where the AV is serving multiple passengers, the AV tunes performance using an aggregate of passenger comfort characteristics based on the passenger profile of each passenger. In other embodiments, the AV tunes the performance based on a priority system and prioritizes passengers with certain passenger profile characteristics over other passengers. In one embodiment, the AV matches passengers according to desired ride comfort. In certain embodiments, comfort models that have lower acceptance by passengers may be deleted or modified.

In one embodiment, the AV utilizes chatbots installed in the AV to track comfort or affect passenger comfort. The chatbots communicate some or all of the AV's decision making with the passengers and get feedback relating to passenger comfort.

In an embodiment, measures for controlling the actuators of an AV based on determined load characteristics are disclosed. Examples of load characteristics include a weight of at least one passenger of the vehicle, the weight of a cargo load of the vehicle, the weight of a hauled cargo attachment, characteristics specifying one or more passenger seating locations, characteristics specifying seatbelt usage information of one or more passengers, characteristics specifying one or more passenger features, and characteristics specifying one or more object shapes.

In an embodiment, the load characteristics are measured by one or more sensors. Examples of the types of sensors used to measure the load characteristics include LiDAR sensors, radar sensors, load sensors, capacitive sensors, inductive sensors, and force sensors. In an embodiment, one or more control attributes of the AV are affected based on the measured load characteristics. Examples of control attributes include throttle, heading, suspension level, suspension stiffness, and the applied torque of at least one wheel of the AV.

In particular, systems, and an apparatus are disclosed for design and operation of a vehicle to increase passenger comfort measured by passenger sensors.

System Overview

FIG. 1 illustrates an example of an autonomous vehicle 100 having autonomous capability.

As used herein, the term "autonomous capability" refers to a function, feature, or facility that enables a vehicle to be partially or fully operated without real-time human intervention, including without limitation fully autonomous vehicles, highly autonomous vehicles, and conditionally autonomous vehicles.

As used herein, an autonomous vehicle (AV) is a vehicle that possesses autonomous capability.

As used herein, "vehicle" includes means of transposition of goods or people. For example, cars, buses, trains, airplanes, drones, trucks, boats, ships, submersibles, dirigibles, etc. A driverless car is an example of an AV.

As used herein, a "road" is a physical area that can be traversed by a vehicle, and may correspond to a named thoroughfare (e.g., city street, interstate freeway, etc.) or may correspond to an unnamed thoroughfare (e.g., a driveway in a house or office building, a section of a parking lot, a section of a vacant lot, a dirt path in a rural area, etc.).

As used herein, a "lane" is a portion of a road that can be traversed by a vehicle, and may correspond to most or all of the space between lane markings, or may correspond to only some (e.g., less than 50%) of the space between lane markings. For example, a road having lane markings spaced far apart might accommodate two or more vehicles between the markings, such that one vehicle can pass the other without traversing the lane markings, and thus could be interpreted as having two lanes between the lane markings.

A lane may also be independent of the markings. For example, if another vehicle is temporarily parked ahead of a navigating vehicle and is occupying a portion of a marked lane in which the navigating vehicle is driving, a new "lane" may be defined to be the remaining portion of the marked lane and a portion of an adjacent marked lane.

As used herein, "trajectory" refers to a path or route to navigate an AV from a first spatiotemporal location to second spatiotemporal location. In an embodiment, the first spatiotemporal location is referred to as the initial or starting location and the second spatiotemporal location is referred to as the destination, final location, goal, goal position, or goal location. In some examples, a trajectory is made up of one or more segments (e.g., sections of road) and each segment is made up of one or more blocks (e.g., portions of a lane or intersection). In an embodiment, the spatiotemporal locations correspond to real world locations. For example, the spatiotemporal locations are pick up or drop-off locations to pick up or drop-off persons or goods.

As used herein, "sensor" includes one or more physical components that detect data about the environment surrounding the physical components. Some of the physical components can include electronic components such as analog-to-digital converters, a buffer (such as a RAM and/or a nonvolatile storage) as well as data processing components such as an ASIC (application-specific integrated circuit), a microprocessor and/or a microcontroller.

"One or more" includes a function being performed by one element, a function being performed by more than one element, e.g., in a distributed fashion, several functions being performed by one element, several functions being performed by several elements, or any combination of the above.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

The terminology used in the description of the various described embodiments herein is for the purpose of describing particular embodiments only and is not intended to be limiting. As used in the description of the various described embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this description, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

As used herein, an AV system refers to the AV along with the array of hardware, software, stored data, and data generated in real-time that supports the operation of the AV. In an embodiment, the AV system is incorporated within the AV. In an embodiment, the AV system is spread across several locations. For example, some of the software of the AV system is implemented on a cloud computing environment similar to cloud computing environment 300 described below with reference to FIG. 3.

In general, this document describes technologies applicable to any vehicles that have one or more autonomous capabilities including fully autonomous vehicles, highly autonomous vehicles, and conditionally autonomous vehicles, such as so-called Level 5, Level 4 and Level 3 vehicles, respectively (see SAE International's standard J3016: Taxonomy and Definitions for Terms Related to On-Road Motor Vehicle Automated Driving Systems, which is incorporated by reference in its entirety, for more details on the classification of levels of autonomy in vehicles). The technologies described in this document are also applicable to partially autonomous vehicles and driver assisted vehicles, such as so-called Level 2 and Level 1 vehicles (see SAE International's standard J3016: Taxonomy and Definitions for Terms Related to On-Road Motor Vehicle Automated Driving Systems). In an embodiment, one or more of the Level 1, 2, 3, 4 and 5 vehicle systems may automate certain vehicle operations (e.g., steering, braking, and using maps) under certain operating conditions based on processing of sensor inputs. The technologies described in this document can benefit vehicles in any levels, ranging from fully autonomous vehicles to human-operated vehicles.

Referring to FIG. 1, an AV system 120 operates the AV 100 autonomously or semi-autonomously along a trajectory 198 through an environment 190 to a destination 199 (sometimes referred to as a final location) while avoiding objects (e.g., natural obstructions 191, vehicles 193, pedestrians 192, cyclists, and other obstacles) and obeying rules of the road (e.g., rules of operation or driving preferences).

In an embodiment, the AV system 120 includes devices 101 that are instrumented to receive and act on operational commands from the computer processors 146. In an embodiment, computing processors 146 are similar to the processor 304 described below in reference to FIG. 3. Examples of devices 101 include a steering control 102, brakes 103, gears, accelerator pedal or other acceleration control mechanisms, windshield wipers, side-door locks, window controls, and turn-indicators.

In an embodiment, the AV system 120 includes sensors 121 for measuring or inferring properties of state or condition of the AV 100, such as the AV's position, linear and angular velocity and acceleration, and heading (e.g., an orientation of the leading end of AV 100). Example of sensors 121 are GNSS, inertial measurement units (IMU) that measure both vehicle linear accelerations and angular rates, wheel speed sensors for measuring or estimating wheel slip ratios, wheel brake pressure or braking torque sensors, engine torque or wheel torque sensors, and steering angle and angular rate sensors.

In an embodiment, the sensors 121 also include sensors for sensing or measuring properties of the AV's environment. For example, monocular or stereo video cameras 122 in the visible light, infrared or thermal (or both) spectra, LiDAR 123, radar, ultrasonic sensors, time-of-flight (TOF)

depth sensors, speed sensors, temperature sensors, humidity sensors, and precipitation sensors.

In an embodiment, the AV system 120 includes a data storage unit 142 and memory 144 for storing machine instructions associated with computer processors 146 or data collected by sensors 121. In an embodiment, the data storage unit 142 is similar to the ROM 308 or storage device 310 described below in relation to FIG. 3. In an embodiment, memory 144 is similar to the main memory 306 described below. In an embodiment, the data storage unit 142 and memory 144 store historical, real-time, and/or predictive data about the environment 190. In an embodiment, the stored data includes maps, driving performance, traffic congestion updates, a traffic pattern, or weather conditions. In an embodiment, data relating to the environment 190 is transmitted to the AV 100 via a communications channel from a remotely located database 134.

In an embodiment, the AV system 120 includes communications devices 140 for communicating measured or inferred properties of other vehicles' states and conditions, such as positions, linear and angular velocities, linear and angular accelerations, and linear and angular headings to the AV 100. These devices include Vehicle-to-Vehicle (V2V) and Vehicle-to-Infrastructure (V2I) communication devices and devices for wireless communications over point-to-point or ad hoc networks or both. In an embodiment, the communications devices 140 communicate across the electromagnetic spectrum (including radio and optical communications) or other media (e.g., air and acoustic media). A combination of Vehicle-to-Vehicle (V2V) Vehicle-to-Infrastructure (V2I) communication (and, in some embodiments, one or more other types of communication) is sometimes referred to as Vehicle-to-Everything (V2X) communication. V2X communication typically conforms to one or more communications standards for communication with, between, and among autonomous vehicles.

In an embodiment, the communication devices 140 include communication interfaces. For example, wired, wireless, WiMAX, Wi-Fi, Bluetooth, satellite, cellular, optical, near field, infrared, or radio interfaces. The communication interfaces transmit data from a remotely located database 134 to AV system 120. In an embodiment, the remotely located database 134 is embedded in a cloud computing environment 200 as described in FIG. 2. The communication interfaces 140 transmit data collected from sensors 121 or other data related to the operation of AV 100 to the remotely located database 134. In an embodiment, communication interfaces 140 transmit data that relates to teleoperations to the AV 100. In some embodiments, the AV 100 communicates with other remote (e.g., "cloud") servers 136.

In an embodiment, the remotely located database 134 also stores and transmits digital data (e.g., storing data such as road and street locations). Such data is stored on the memory 144 on the AV 100, or transmitted to the AV 100 via a communications channel from the remotely located database 134.

In an embodiment, the remotely located database 134 stores and transmits historical data about driving properties (e.g., speed and acceleration profiles) of vehicles that have previously traveled along trajectory 198 at similar times of day. In one implementation, such data may be stored on the memory 144 on the AV 100, or transmitted to the AV 100 via a communications channel from the remotely located database 134.

Computing devices 146 located on the AV 100 algorithmically generate control actions based on both real-time sensor data and prior data, allowing the AV system 120 to execute its autonomous driving capabilities.

In an embodiment, the AV system 120 includes computer peripherals 132 coupled to computing devices 146 for providing data and alerts to, and receiving input from, a user (e.g., an occupant or a remote user) of the AV 100. In an embodiment, peripherals 132 are similar to the display 312, input device 314, and cursor controller 316 discussed below in reference to FIG. 3. The coupling is wireless or wired. Any two or more of the interface devices may be integrated into a single device.

Cloud Computing Environment

Figure 2:
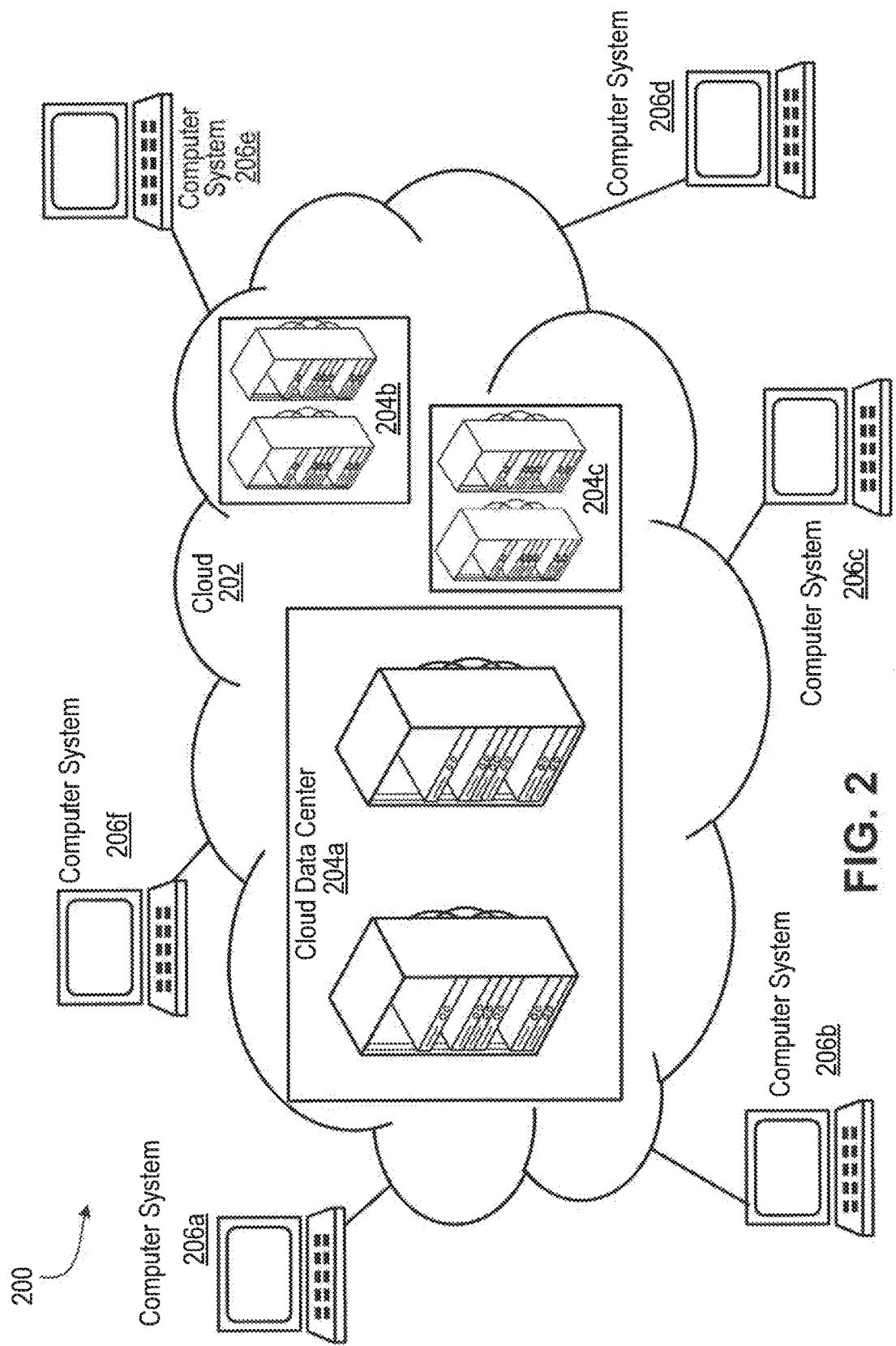
FIG. 2 illustrates an exemplary "cloud" computing environment, in accordance with one or more embodiments.

FIG. 2 illustrates an exemplary "cloud" computing environment. Cloud computing is a model of service delivery for enabling convenient, on-demand network access to a shared pool of configurable computing resources (e.g. networks, network bandwidth, servers, processing, memory, storage, applications, virtual machines, and services). In typical cloud computing systems, one or more large cloud data centers house the machines used to deliver the services provided by the cloud. Referring now to FIG. 2, the cloud computing environment 200 includes cloud data centers 204a, 204b, and 204c that are interconnected through the cloud 202. Data centers 204a, 204b, and 204c provide cloud computing services to computer systems 206a, 206b, 206c, 206d, 206e, and 206f connected to cloud 202.

The cloud computing environment 200 includes one or more cloud data centers. In general, a cloud data center, for example the cloud data center 204a shown in FIG. 2, refers to the physical arrangement of servers that make up a cloud, for example the cloud 202 shown in FIG. 2, or a particular portion of a cloud. For example, servers are physically arranged in the cloud datacenter into rooms, groups, rows, and racks. A cloud datacenter has one or more zones, which include one or more rooms of servers. Each room has one or more rows of servers, and each row includes one or more racks. Each rack includes one or more individual server nodes. In some implementation, servers in zones, rooms, racks, and/or rows are arranged into groups based on physical infrastructure requirements of the datacenter facility, which include power, energy, thermal, heat, and/or other requirements. In an embodiment, the server nodes are similar to the computer system described in FIG. 3. The data center 204a has many computing systems distributed through many racks.

The cloud 202 includes cloud data centers 204a, 204b, and 204c along with the network and networking resources (for example, networking equipment, nodes, routers, switches, and networking cables) that interconnect the cloud data centers 204a, 204b, and 204c and help facilitate the computing systems' 206a-f access to cloud computing services. In an embodiment, the network represents any combination of one or more local networks, wide area networks, or internetworks coupled using wired or wireless links deployed using terrestrial or satellite connections. Data exchanged over the network, is transferred using any number of network layer protocols, such as Internet Protocol (IP), Multiprotocol Label Switching (MPLS), Asynchronous Transfer Mode (ATM), Frame Relay, etc. Furthermore, in embodiments where the network represents a combination of multiple sub-networks, different network layer protocols are used at each of the underlying sub-networks. In some embodiments, the network represents one or more interconnected internetworks, such as the public Internet.

The computing systems 206a-f or cloud computing services consumers are connected to the cloud 202 through network links and network adapters. In an embodiment, the computing systems 206a-f are implemented as various computing devices, for example servers, desktops, laptops, tablet, smartphones, IoT devices, autonomous vehicles (including, cars, drones, shuttles, trains, buses, etc.) and consumer electronics. In an embodiment, the computing systems 206a-f are implemented in or as a part of other systems.

Computer System

Figure 3:
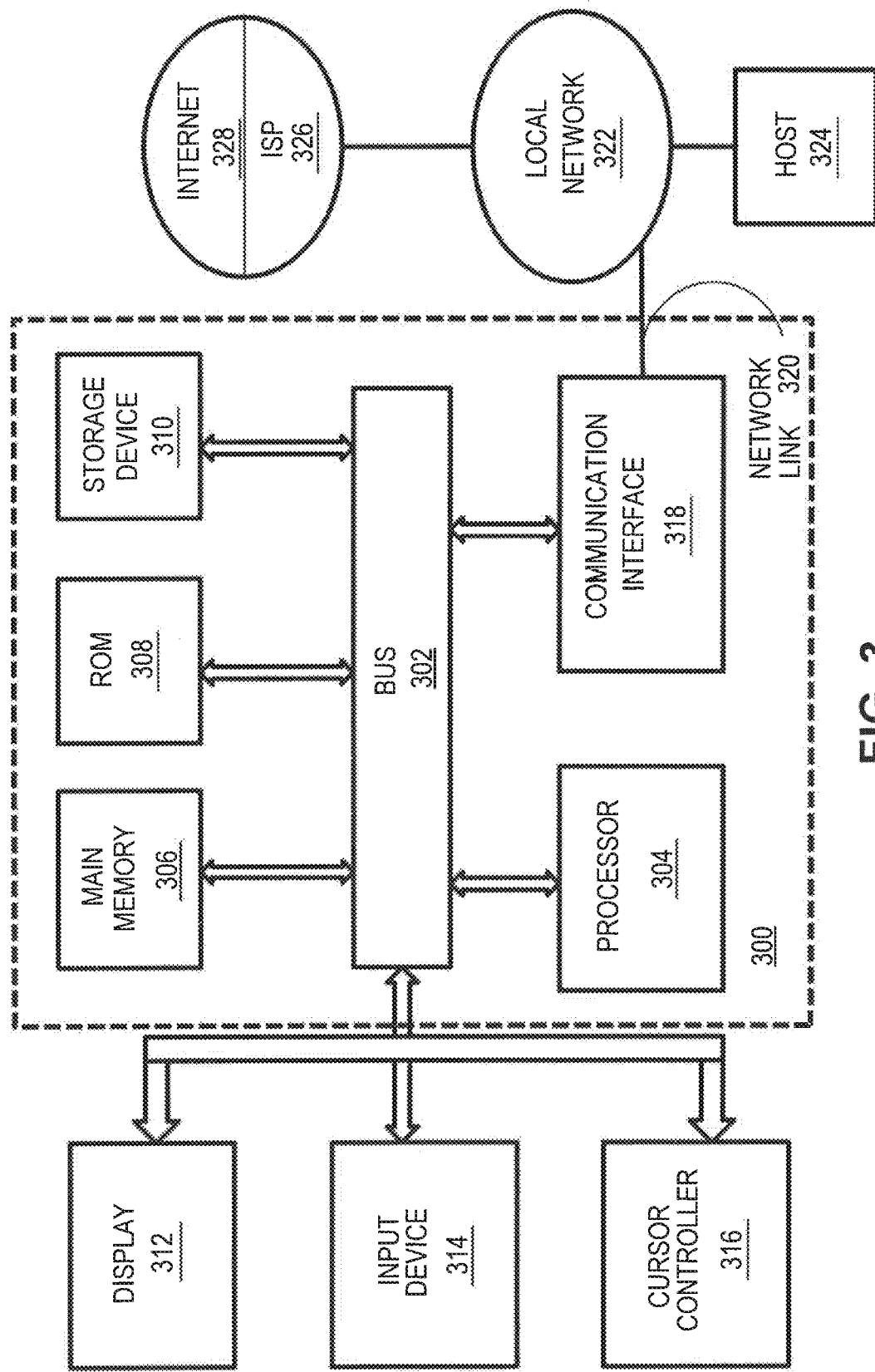
FIG. 3 illustrates a computer system, in accordance with one or more embodiments.

FIG. 3 illustrates a computer system 300. In an implementation, the computer system 300 is a special purpose computing device. The special-purpose computing device is hard-wired to perform the techniques or includes digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. In various embodiments, the special-purpose computing devices are desktop computer systems, portable computer systems, handheld devices, network devices or any other device that incorporates hard-wired and/or program logic to implement the techniques.

In an embodiment, the computer system 300 includes a bus 302 or other communication mechanism for communicating data, and a hardware processor 304 coupled with a bus 302 for processing data. The hardware processor 304 is, for example, a general-purpose microprocessor. The computer system 300 also includes a main memory 306, such as a random-access memory (RAM) or other dynamic storage device, coupled to the bus 302 for storing data and instructions to be executed by processor 304. In one implementation, the main memory 306 is used for storing temporary variables or other intermediate data during execution of instructions to be executed by the processor 304. Such instructions, when stored in non-transitory storage media accessible to the processor 304, render the computer system 300 into a special-purpose machine that is customized to perform the operations specified in the instructions.

In an embodiment, the computer system 300 further includes a read only memory (ROM) 308 or other static storage device coupled to the bus 302 for storing static data and instructions for the processor 304. A storage device 310, such as a magnetic disk, optical disk, solid-state drive, or three-dimensional cross point memory is provided and coupled to the bus 302 for storing data and instructions.

In an embodiment, the computer system 300 is coupled via the bus 302 to a display 312, such as a cathode ray tube (CRT), a liquid crystal display (LCD), plasma display, light emitting diode (LED) display, or an organic light emitting diode (OLED) display for displaying data to a computer user. An input device 314, including alphanumeric and other keys, is coupled to bus 302 for communicating data and command selections to the processor 304. Another type of user input device is a cursor controller 316, such as a mouse, a trackball, a touch-enabled display, or cursor direction keys for communicating direction data and command selections to the processor 304 and for controlling cursor movement on the display 312. This input device typically has two degrees of freedom in two axes, a first axis (e.g., x-axis) and a second axis (e.g., y-axis), that allows the device to specify positions in a plane.

According to one embodiment, the techniques herein are performed by the computer system 300 in response to the processor 304 executing one or more sequences of one or more instructions contained in the main memory 306. Such instructions are read into the main memory 306 from another storage medium, such as the storage device 310. Execution of the sequences of instructions contained in the main memory 306 causes the processor 304 to perform the process steps described herein. In alternative embodiments, hard-wired circuitry is used in place of or in combination with software instructions.

The term "storage media" as used herein refers to any non-transitory media that store data and/or instructions that cause a machine to operate in a specific fashion. Such storage media includes non-volatile media and/or volatile media. Non-volatile media includes, for example, optical disks, magnetic disks, solid-state drives, or three-dimensional cross point memory, such as the storage device 310. Volatile media includes dynamic memory, such as the main memory 306. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NV-RAM, or any other memory chip or cartridge.

Storage media is distinct from but may be used in conjunction with transmission media. Transmission media participates in transferring data between storage media. For example, transmission media includes coaxial cables, copper wire and fiber optics, including the wires that include the bus 302. Transmission media can also take the form of acoustic or light waves, such as those generated during radio-wave and infrared data communications.

In an embodiment, various forms of media are involved in carrying one or more sequences of one or more instructions to the processor 304 for execution. For example, the instructions are initially carried on a magnetic disk or solid-state drive of a remote computer. The remote computer loads the instructions into its dynamic memory and send the instructions over a telephone line using a modem. A modem local to the computer system 300 receives the data on the telephone line and use an infrared transmitter to convert the data to an infrared signal. An infrared detector receives the data carried in the infrared signal and appropriate circuitry places the data on the bus 302. The bus 302 carries the data to the main memory 306, from which processor 304 retrieves and executes the instructions. The instructions received by the main memory 306 may optionally be stored on the storage device 310 either before or after execution by processor 304.

The computer system 300 also includes a communication interface 318 coupled to the bus 302. The communication interface 318 provides a two-way data communication coupling to a network link 320 that is connected to a local network 322. For example, the communication interface 318 is an integrated service digital network (ISDN) card, cable modem, satellite modem, or a modem to provide a data communication connection to a corresponding type of telephone line. As another example, the communication interface 318 is a local area network (LAN) card to provide a data communication connection to a compatible LAN. In some implementations, wireless links are also implemented. In any such implementation, the communication interface 318 sends and receives electrical, electromagnetic, or optical signals that carry digital data streams representing various types of data.

The network link 320 typically provides data communication through one or more networks to other data devices. For example, the network link 320 provides a connection through the local network 322 to a host computer 324 or to a cloud data center or equipment operated by an Internet Service Provider (ISP) 326. The ISP 326 in turn provides data communication services through the world-wide packet data communication network now commonly referred to as the "Internet" 328. The local network 322 and Internet 328 both use electrical, electromagnetic or optical signals that carry digital data streams. The signals through the various networks and the signals on the network link 320 and through the communication interface 318, which carry the digital data to and from the computer system 300, are example forms of transmission media. In an embodiment, the network 322 contains the cloud 202 or a part of the cloud 202 described above.

The computer system 300 sends messages and receives data, including program code, through the network(s), the network link 320, and the communication interface 318. In an embodiment, the computer system 300 receives code for processing. The received code is executed by the processor 304 as it is received, and/or stored in storage device 310, or other non-volatile storage for later execution.

Autonomous Vehicle Architecture

Figure 4:
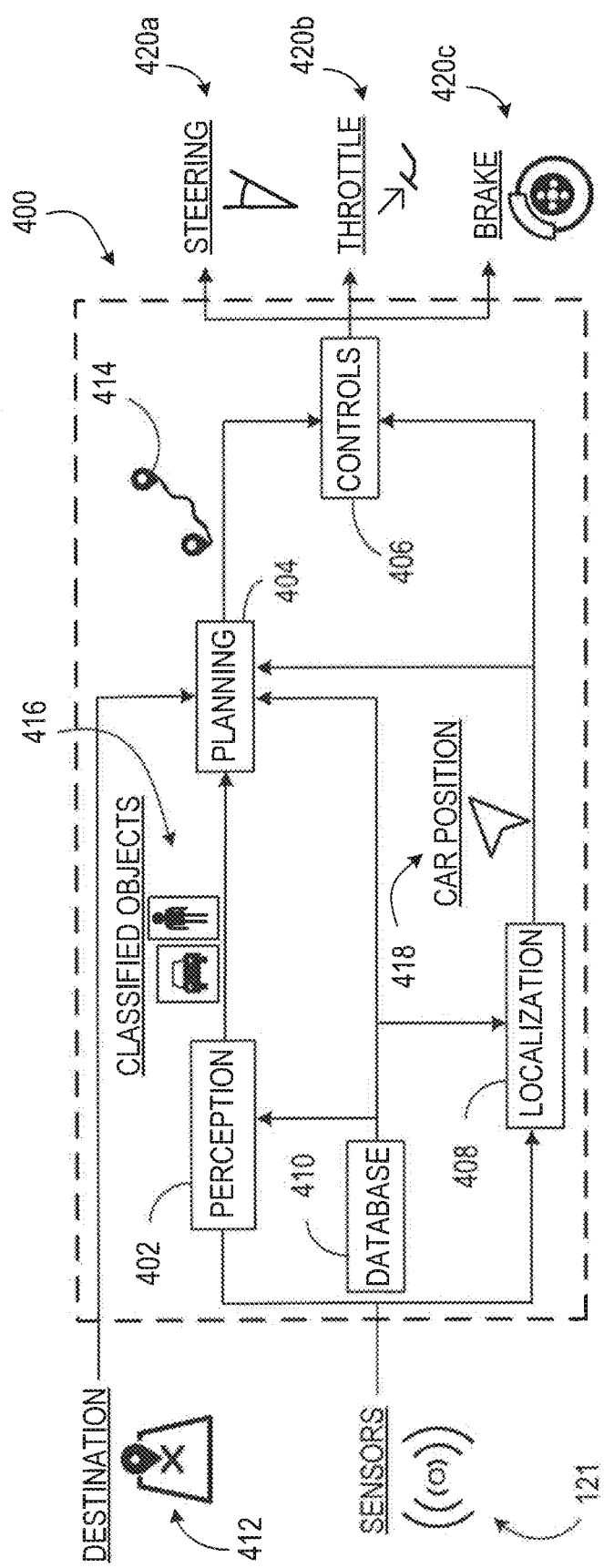
FIG. 4 illustrates an example architecture for an AV, in accordance with one or more embodiments.

FIG. 4 illustrates an example architecture 400 for an autonomous vehicle (e.g., the AV 100 shown in FIG. 1). The architecture 400 includes a perception module 402 (sometimes referred to as a perception circuit), a planning module 404 (sometimes referred to as a planning circuit), a control module 406 (sometimes referred to as a control circuit), a localization module 408 (sometimes referred to as a localization circuit), and a database module 410 (sometimes referred to as a database circuit). Each module plays a role in the operation of the AV 100. Together, the modules 402, 404, 406, 408, and 410 may be part of the AV system 120 shown in FIG. 1. In some embodiments, any of the modules 402, 404, 406, 408, and 410 is a combination of computer software (e.g., executable code stored on a computer-readable medium) and computer hardware (e.g., one or more microprocessors, microcontrollers, application-specific integrated circuits [ASICs]), hardware memory devices, other types of integrated circuits, other types of computer hardware, or a combination of any or all of these things).

In use, the planning module 404 receives data representing a destination 412 and determines data representing a trajectory 414 (sometimes referred to as a route) that can be traveled by the AV 100 to reach (e.g., arrive at) the destination 412. In order for the planning module 404 to determine the data representing the trajectory 414, the planning module 404 receives data from the perception module 402, the localization module 408, and the database module 410.

The perception module 402 identifies nearby physical objects using one or more sensors 121, e.g., as also shown in FIG. 1. The objects are classified (e.g., grouped into types such as pedestrian, bicycle, automobile, traffic sign, etc.) and data representing the classified objects 416 is provided to the planning module 404.

The planning module 404 also receives data representing the AV position 418 from the localization module 408. The localization module 408 determines the AV position by using data from the sensors 121 and data from the database module 410 (e.g., a geographic data) to calculate a position. For example, the localization module 408 uses data from a GNSS sensor and geographic data to calculate a longitude and latitude of the AV. In an embodiment, data used by the localization module 408 includes high-precision maps of the roadway geometric properties, maps describing road network connectivity properties, maps describing roadway physical properties (such as traffic speed, traffic volume, the number of vehicular and cyclist traffic lanes, lane width, lane traffic directions, or lane marker types and locations, or combinations of them), and maps describing the spatial locations of road features such as crosswalks, traffic signs or other travel signals of various types.

The control module 406 receives the data representing the trajectory 414 and the data representing the AV position 418 and operates the control functions 420a-c (e.g., steering, throttling, braking, ignition) of the AV in a manner that will cause the AV 100 to travel the trajectory 414 to the destination 412. For example, if the trajectory 414 includes a left turn, the control module 406 will operate the control functions 420a-c in a manner such that the steering angle of the steering function will cause the AV 100 to turn left and the throttling and braking will cause the AV 100 to pause and wait for passing pedestrians or vehicles before the turn is made.

Autonomous Vehicle Inputs

Figure 5:
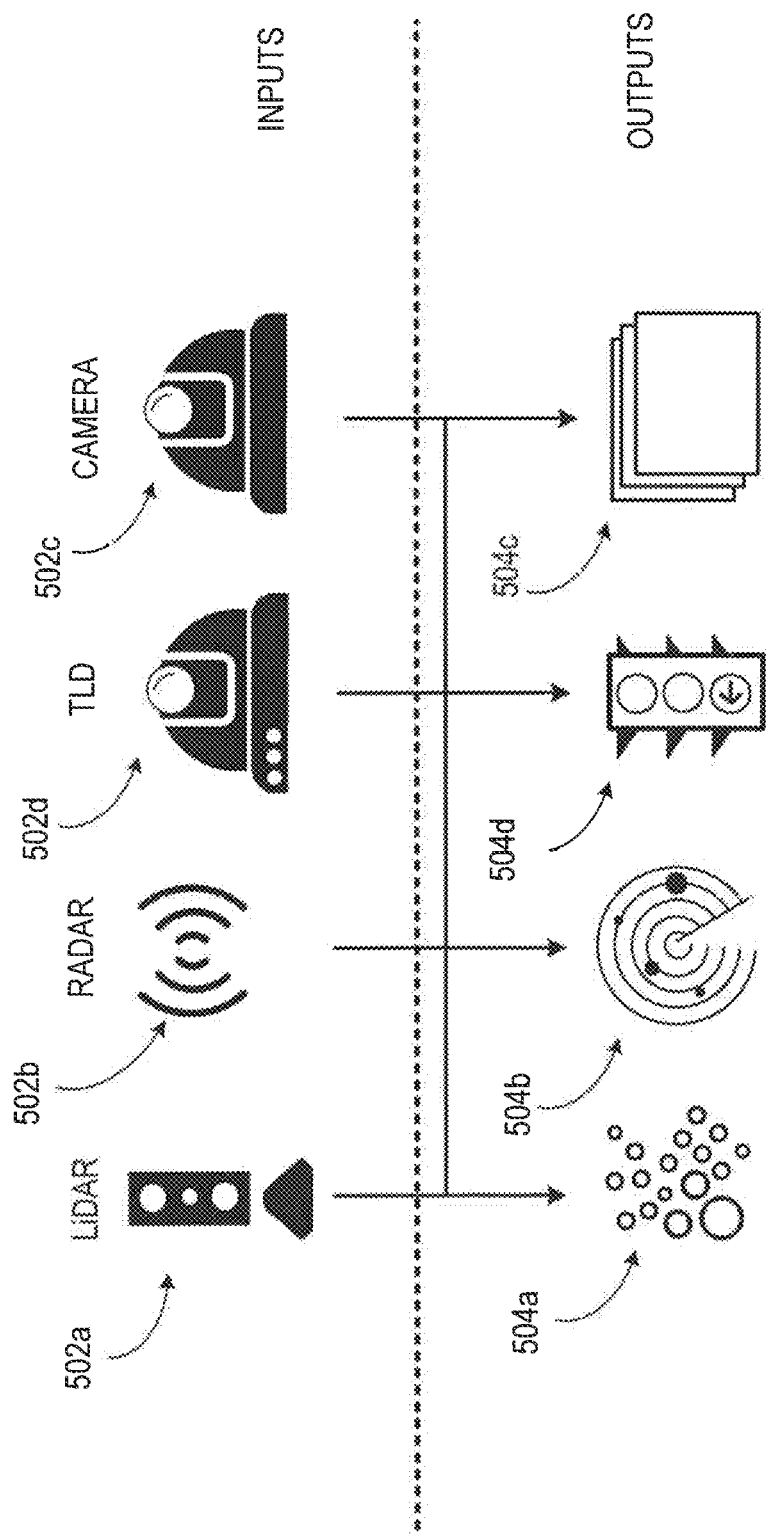
FIG. 5 illustrates an example of inputs and outputs that may be used by a perception module, in accordance with one or more embodiments.

FIG. 5 illustrates an example of inputs 502a-d (e.g., sensors 121 shown in FIG. 1) and outputs 504a-d (e.g., sensor data) that is used by the perception module 402 (FIG. 4). One input 502a is a LiDAR (Light Detection And Ranging) system (e.g., LiDAR 123 shown in FIG. 1). LiDAR is a technology that uses light (e.g., bursts of light such as infrared light) to obtain data about physical objects in its line of sight. A LiDAR system produces LiDAR data as output 504a. For example, LiDAR data is collections of 3D or 2D points (also known as a point clouds) that are used to construct a representation of the environment 190.

Another input 502b is a radar system. Radar is a technology that uses radio waves to obtain data about nearby physical objects. Radars can obtain data about objects not within the line of sight of a LiDAR system. A radar system 502b produces radar data as output 504b. For example, radar data are one or more radio frequency electromagnetic signals that are used to construct a representation of the environment 190.

Another input 502c is a camera system. A camera system uses one or more cameras (e.g., digital cameras using a light sensor such as a charge-coupled device [CCD]) to obtain data about nearby physical objects. A camera system produces camera data as output 504c. Camera data often takes the form of image data (e.g., data in an image data format such as RAW, JPEG, PNG, etc.). In some examples, the camera system has multiple independent cameras, e.g., for the purpose of stereopsis (stereo vision), which enables the camera system to perceive depth. Although the objects perceived by the camera system are described here as "nearby," this is relative to the AV. In use, the camera system may be configured to "see" objects far, e.g., up to a kilometer or more ahead of the AV. Accordingly, the camera system may have features such as sensors and lenses that are optimized for perceiving objects that are far away.

Another input 502d is a traffic light detection (TLD) system. A TLD system uses one or more cameras to obtain data about traffic lights, street signs, and other physical objects that provide visual navigation data. A TLD system produces TLD data as output 504d. TLD data often takes the form of image data (e.g., data in an image data format such as RAW, JPEG, PNG, etc.). A TLD system differs from a system incorporating a camera in that a TLD system uses a camera with a wide field of view (e.g., using a wide-angle lens or a fish-eye lens) in order to obtain data about as many physical objects providing visual navigation data as possible, so that the AV 100 has access to all relevant navigation data provided by these objects. For example, the viewing angle of the TLD system may be about 120 degrees or more.

In some embodiments, outputs 504a-d are combined using a sensor fusion technique. Thus, either the individual outputs 504a-d are provided to other systems of the AV 100 (e.g., provided to a planning module 404 as shown in FIG. 4), or the combined output can be provided to the other systems, either in the form of a single combined output or multiple combined outputs of the same type (e.g., using the same combination technique or combining the same outputs or both) or different types type (e.g., using different respective combination techniques or combining different respective outputs or both). In some embodiments, an early fusion technique is used. An early fusion technique is characterized by combining outputs before one or more data processing steps are applied to the combined output. In some embodiments, a late fusion technique is used. A late fusion technique is characterized by combining outputs after one or more data processing steps are applied to the individual outputs.

Example of a LiDAR System

Figure 6:
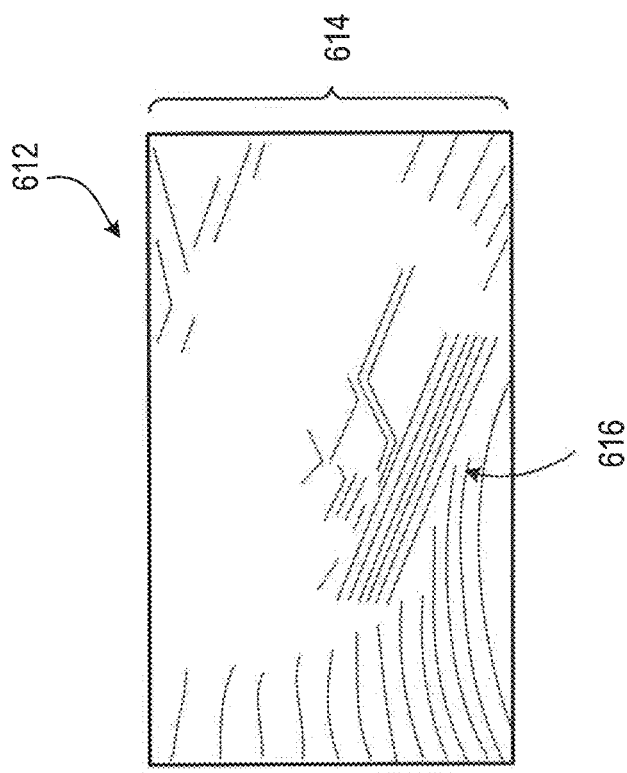
FIG. 6 illustrates an example of a LiDAR system, in accordance with one or more embodiments.
Figure 6:
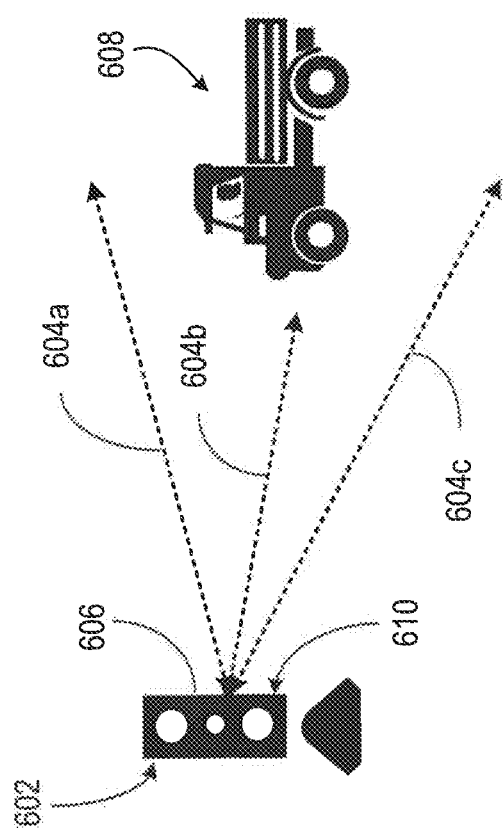

FIG. 6 illustrates an example of a LiDAR system 602 (e.g., the input 502a shown in FIG. 5). The LiDAR system 602 emits light 604a-c from a light emitter 606 (e.g., a laser transmitter). Light emitted by a LiDAR system is typically not in the visible spectrum; for example, infrared light is often used. Some of the light 604b emitted encounters a physical object 608 (e.g., a vehicle) and reflects back to the LiDAR system 602. (Light emitted from a LiDAR system typically does not penetrate physical objects, e.g., physical objects in solid form.) The LiDAR system 602 also has one or more light detectors 610, which detect the reflected light. In an embodiment, one or more data processing systems associated with the LiDAR system generates an image 612 representing the field of view 614 of the LiDAR system. The image 612 includes data that represents the boundaries 616 of a physical object 608. In this way, the image 612 is used to determine the boundaries 616 of one or more physical objects near an AV.

LiDAR System in Operation

Figure 7:
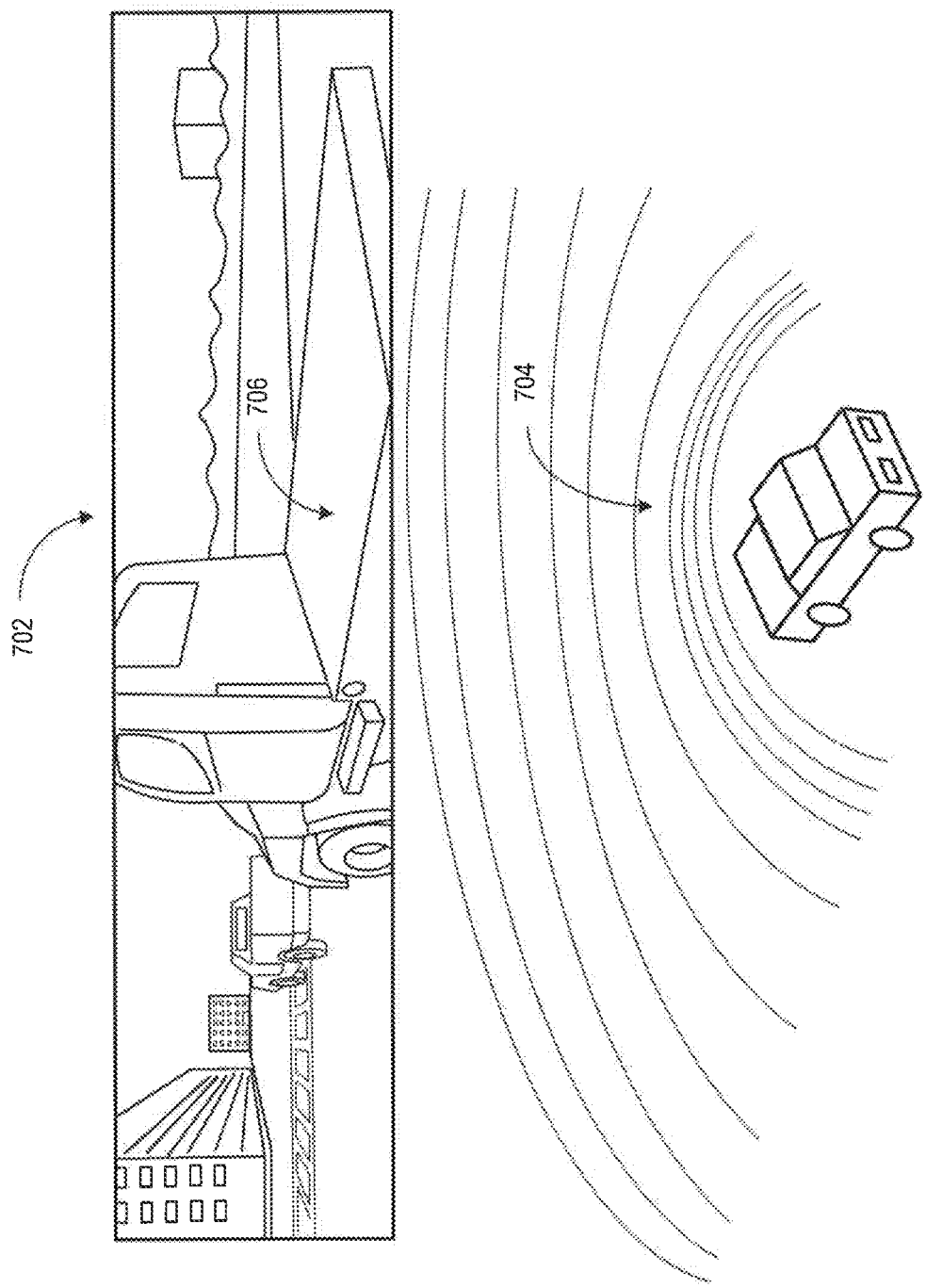
FIG. 7 illustrates the LiDAR system in operation, in accordance with one or more embodiments.

FIG. 7 illustrates the LiDAR system 602 in operation. In the scenario shown in this figure, the AV 100 receives both camera system output 504c in the form of an image 702 and LiDAR system output 504a in the form of LiDAR data points 704. In use, the data processing systems of the AV 100 compares the image 702 to the data points 704. In particular, a physical object 706 identified in the image 702 is also identified among the data points 704. In this way, the AV 100 perceives the boundaries of the physical object based on the contour and density of the data points 704.

Figure 8:
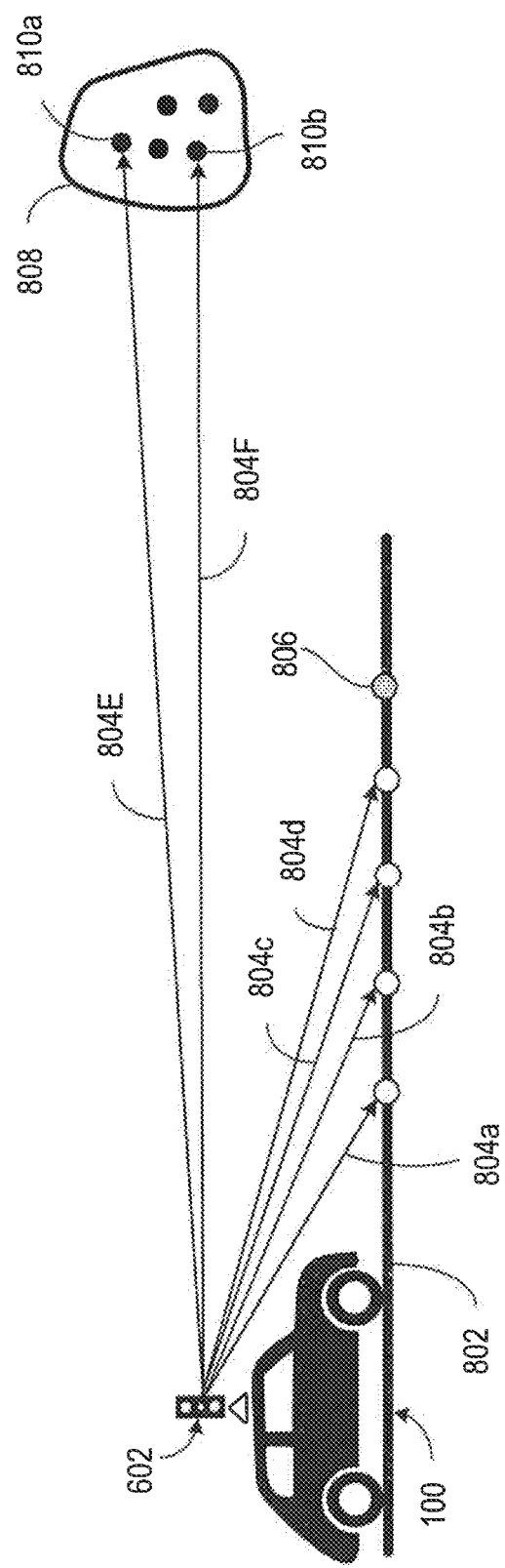
FIG. 8 illustrates the operation of the LiDAR system in additional detail, in accordance with one or more embodiments.

FIG. 8 illustrates the operation of the LiDAR system 602 in additional detail. As described above, the AV 100 detects the boundary of a physical object based on characteristics of the data points detected by the LiDAR system 602. As shown in FIG. 8, a flat object, such as the ground 802, will reflect light 804a-d emitted from a LiDAR system 602 in a consistent manner. Put another way, because the LiDAR system 602 emits light using consistent spacing, the ground 802 will reflect light back to the LiDAR system 602 with the same consistent spacing. As the AV 100 travels over the ground 802, the LiDAR system 602 will continue to detect light reflected by the next valid ground point 806 if nothing is obstructing the road. However, if an object 808 obstructs the road, light 804e-f emitted by the LiDAR system 602 will be reflected from points 810a-b in a manner inconsistent with the expected consistent manner. From this data, the AV 100 can determine that the object 808 is present.

Autonomous Vehicle Planning

Figure 9:
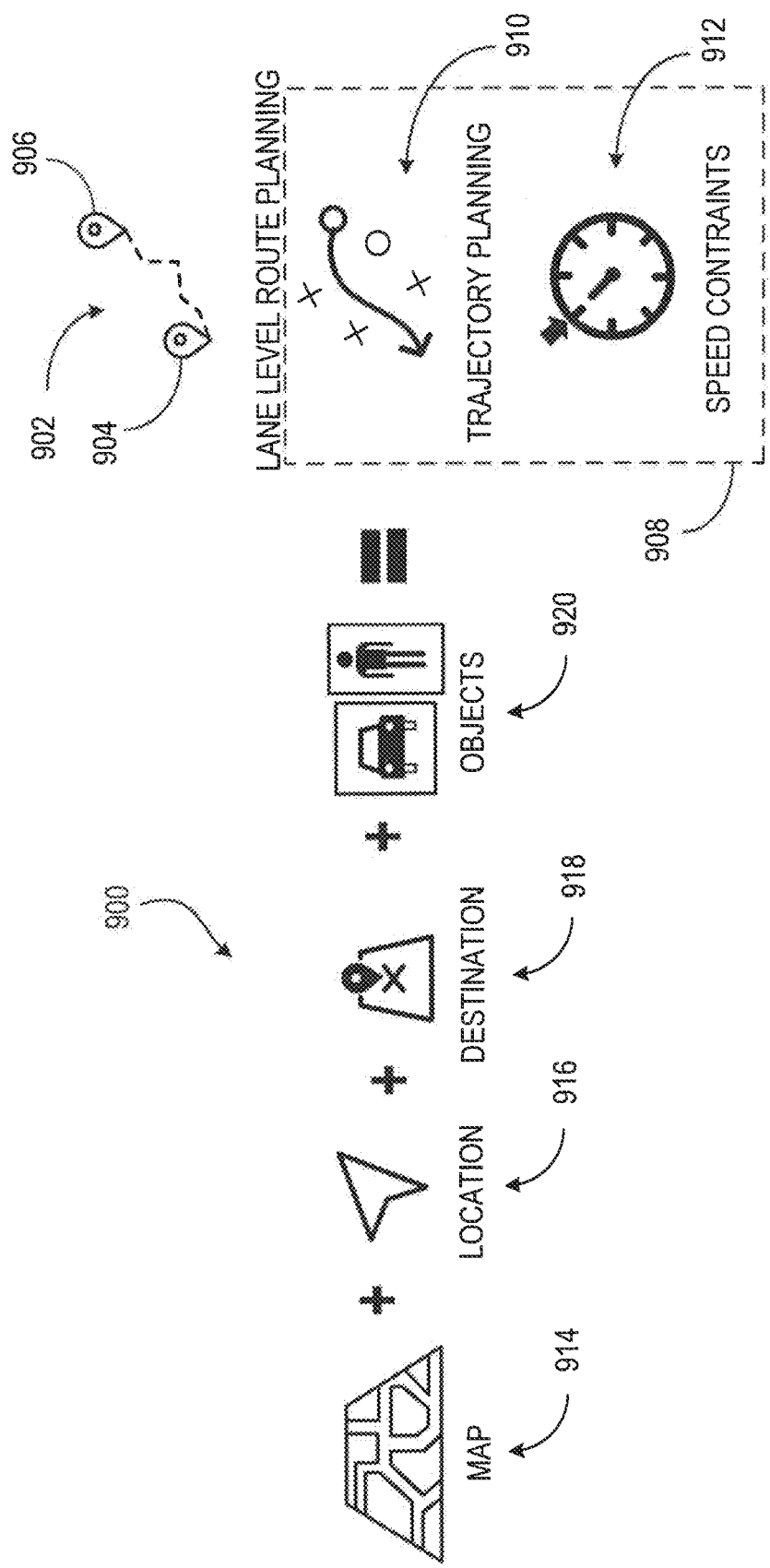
FIG. 9 illustrates a block diagram of the relationships between inputs and outputs of a planning module, in accordance with one or more embodiments.

FIG. 9 illustrates a block diagram 900 of the relationships between inputs and outputs of a planning module 404 (e.g., as shown in FIG. 4). In general, the output of a planning module 404 is a route 902 from a start point 904 (e.g., source location or initial location), and an end point 906 (e.g., destination or final location). The route 902 is typically defined by one or more segments. For example, a segment is a distance to be traveled over at least a portion of a street, road, highway, driveway, or other physical area appropriate for automobile travel. In some examples, e.g., if the AV 100 is an off-road capable vehicle such as a four-wheel-drive (4WD) or all-wheel-drive (AWD) car, SUV, pick-up truck, or the like, the route 902 includes "off-road" segments such as unpaved paths or open fields.

In addition to the route 902, a planning module also outputs lane-level route planning data 908. The lane-level route planning data 908 is used to traverse segments of the route 902 based on conditions of the segment at a particular time. For example, if the route 902 includes a multi-lane highway, the lane-level route planning data 908 includes trajectory planning data 910 that the AV 100 can use to choose a lane among the multiple lanes, e.g., based on whether an exit is approaching, whether one or more of the lanes have other vehicles, or other factors that vary over the course of a few minutes or less. Similarly, in some implementations, the lane-level route planning data 908 includes speed constraints 912 specific to a segment of the route 902. For example, if the segment includes pedestrians or unexpected traffic, the speed constraints 912 may limit the AV 100 to a travel speed slower than an expected speed, e.g., a speed based on speed limit data for the segment.

In an embodiment, the inputs to the planning module 404 includes database data 914 (e.g., from the database module 410 shown in FIG. 4), current location data 916 (e.g., the AV position 418 shown in FIG. 4), destination data 918 (e.g., for the destination 412 shown in FIG. 4), and object data 920 (e.g., the classified objects 416 as perceived by the perception module 402 as shown in FIG. 4). In some embodiments, the database data 914 includes rules used in planning. Rules are specified using a formal language, e.g., using Boolean logic. In any given situation encountered by the AV 100, at least some of the rules will apply to the situation. A rule applies to a given situation if the rule has conditions that are met based on data available to the AV 100, e.g., data about the surrounding environment. Rules can have priority. For example, a rule that says, "if the road is a freeway, move to the leftmost lane" can have a lower priority than "if the exit is approaching within a mile, move to the rightmost lane."

Path Planning

Figure 10:
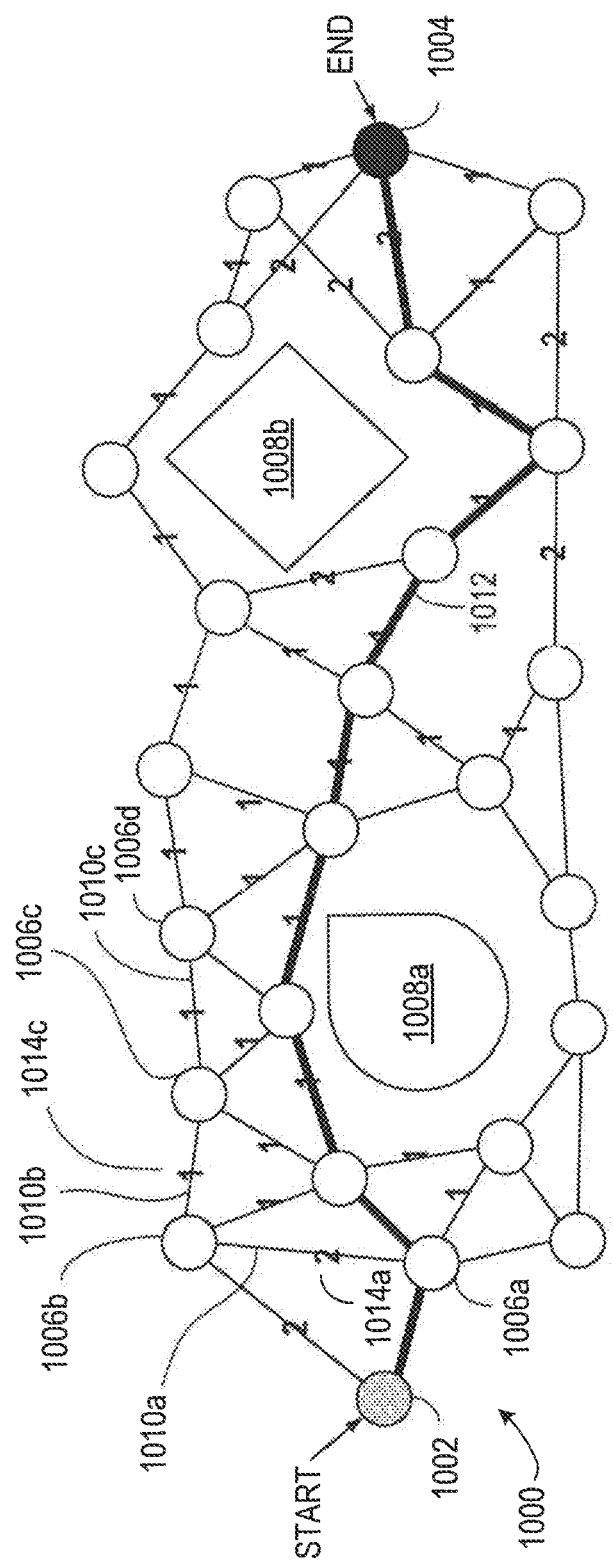
FIG. 10 illustrates a directed graph used in path planning, in accordance with one or more embodiments.

FIG. 10 illustrates a directed graph 1000 used in path planning, e.g., by the planning module 404 (FIG. 4). In general, a directed graph 1000 like the one shown in FIG. 10 is used to determine a path between any start point 1002 and end point 1004. In real-world terms, the distance separating the start point 1002 and end point 1004 may be relatively large (e.g., in two different metropolitan areas) or may be relatively small (e.g., two intersections abutting a city block or two lanes of a multi-lane road).

In an embodiment, the directed graph 1000 has nodes 1006a-d representing different locations between the start point 1002 and the end point 1004 that could be occupied by an AV 100. In some examples, e.g., when the start point 1002 and end point 1004 represent different metropolitan areas, the nodes 1006a-d represent segments of roads. In some examples, e.g., when the start point 1002 and the end point 1004 represent different locations on the same road, the nodes 1006a-d represent different positions on that road. In this way, the directed graph 1000 includes data at varying levels of granularity. In an embodiment, a directed graph having high granularity is also a subgraph of another directed graph having a larger scale. For example, a directed graph in which the start point 1002 and the end point 1004 are far away (e.g., many miles apart) has most of its data at a low granularity and is based on stored data, but also includes some high granularity data for the portion of the graph that represents physical locations in the field of view of the AV 100.

The nodes 1006a-d are distinct from objects 1008a-b which cannot overlap with a node. In an embodiment, when granularity is low, the objects 1008a-b represent regions that cannot be traversed by automobile, e.g., areas that have no streets or roads. When granularity is high, the objects 1008a-b represent physical objects in the field of view of the AV 100, e.g., other automobiles, pedestrians, or other entities with which the AV 100 cannot share physical space. In an embodiment, some or all of the objects 1008a-b are a static objects (e.g., an object that does not change position such as a street lamp or utility pole) or dynamic objects (e.g., an object that is capable of changing position such as a pedestrian or other car).

The nodes 1006a-d are connected by edges 1010a-c. If two nodes 1006a-b are connected by an edge 1010a, it is possible for an AV 100 to travel between one node 1006a and the other node 1006b, e.g., without having to travel to an intermediate node before arriving at the other node 1006b. (When we refer to an AV 100 traveling between nodes, we mean that the AV 100 travels between the two physical positions represented by the respective nodes.) The edges 1010a-c are often bidirectional, in the sense that an AV 100 travels from a first node to a second node, or from the second node to the first node. In an embodiment, edges 1010a-c are unidirectional, in the sense that an AV 100 can travel from a first node to a second node, however the AV 100 cannot travel from the second node to the first node. Edges 1010a-c are unidirectional when they represent, for example, one-way streets, individual lanes of a street, road, or highway, or other features that can only be traversed in one direction due to legal or physical constraints.

In an embodiment, the planning module 404 uses the directed graph 1000 to identify a path 1012 made up of nodes and edges between the start point 1002 and end point 1004.

An edge 1010a-c has an associated cost 1014a-b. The cost 1014a-b is a value that represents the resources that will be expended if the AV 100 chooses that edge. A typical resource is time. For example, if one edge 1010a represents a physical distance that is twice that as another edge 1010b, then the associated cost 1014a of the first edge 1010a may be twice the associated cost 1014b of the second edge 1010b. Other factors that affect time include expected traffic, number of intersections, speed limit, etc. Another typical resource is fuel economy. Two edges 1010a-b may represent the same physical distance, but one edge 1010a may require more fuel than another edge 1010b, e.g., because of road conditions, expected weather, etc.

When the planning module 404 identifies a path 1012 between the start point 1002 and end point 1004, the planning module 404 typically chooses a path optimized for cost, e.g., the path that has the least total cost when the individual costs of the edges are added together.

Autonomous Vehicle Control

Figure 11:
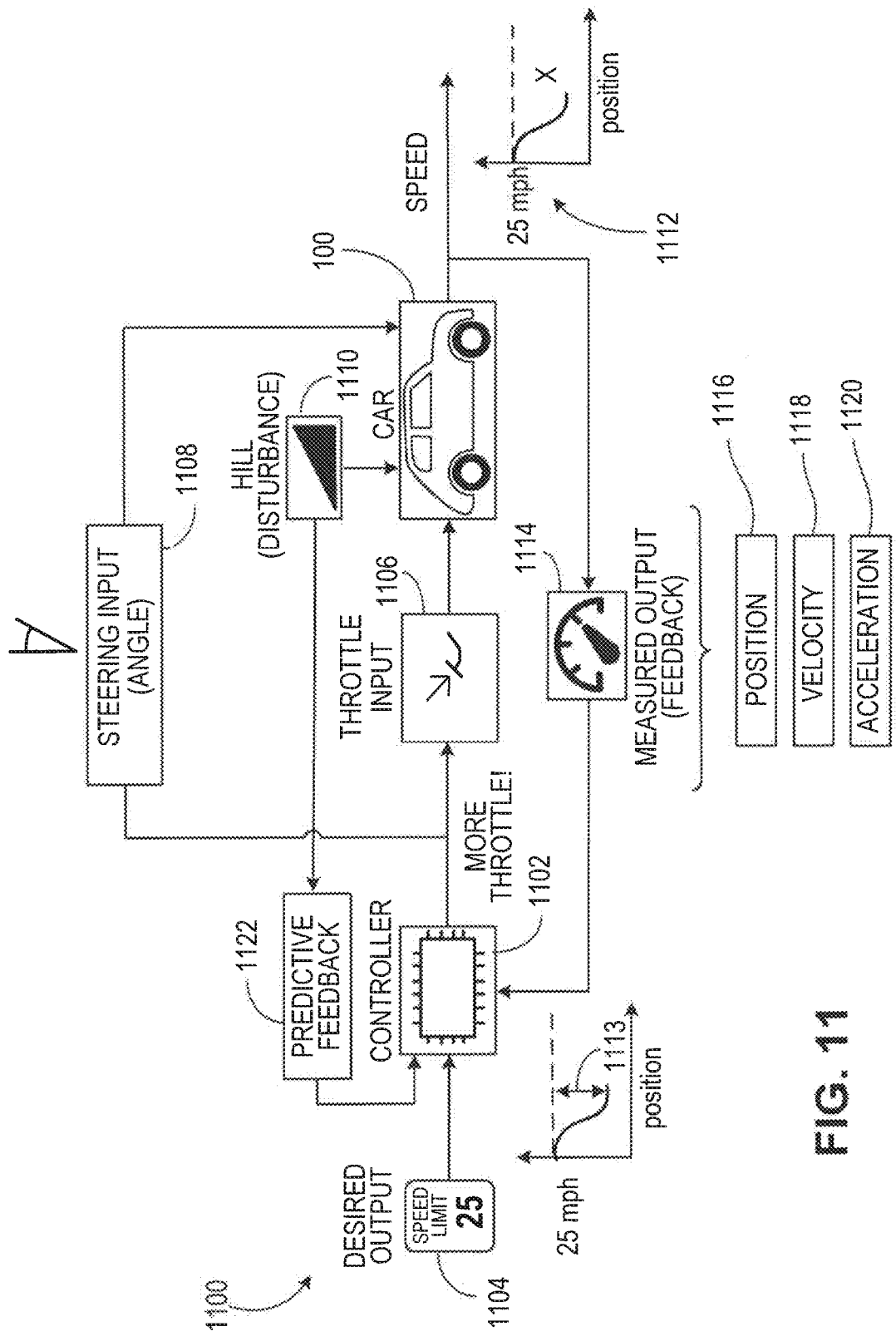
FIG. 11 illustrates a block diagram of the inputs and outputs of a control module, in accordance with one or more embodiments.

FIG. 11 illustrates a block diagram 1100 of the inputs and outputs of a control module 406 (e.g., as shown in FIG. 4). A control module operates in accordance with a controller 1102 which includes, for example, one or more processors (e.g., one or more computer processors such as microprocessors or microcontrollers or both) similar to processor 304, short-term and/or long-term data storage (e.g., memory random-access memory or flash memory or both) similar to main memory 306, ROM 1308, and storage device 210, and instructions stored in memory that carry out operations of the controller 1102 when the instructions are executed (e.g., by the one or more processors).

In an embodiment, the controller 1102 receives data representing a desired output 1104. The desired output 1104 typically includes a velocity, e.g., a speed and a heading. The desired output 1104 can be based on, for example, data received from a planning module 404 (e.g., as shown in FIG. 4). In accordance with the desired output 1104, the controller 1102 produces data usable as a throttle input 1106 and a steering input 1108. The throttle input 1106 represents the magnitude in which to engage the throttle (e.g., acceleration control) of an AV 100, e.g., by engaging the steering pedal, or engaging another throttle control, to achieve the desired output 1104. In some examples, the throttle input 1106 also includes data usable to engage the brake (e.g., deceleration control) of the AV 100. The steering input 1108 represents a steering angle, e.g., the angle at which the steering control (e.g., steering wheel, steering angle actuator, or other functionality for controlling steering angle) of the AV should be positioned to achieve the desired output 1104.

In an embodiment, the controller 1102 receives feedback that is used in adjusting the inputs provided to the throttle and steering. For example, if the AV 100 encounters a disturbance 1110, such as a hill, the measured speed 1112 of the AV 100 is lowered below the desired output speed. In an embodiment, any measured output 1114 is provided to the controller 1102 so that the necessary adjustments are performed, e.g., based on the differential 1113 between the measured speed and desired output. The measured output 1114 includes measured position 1116, measured velocity 1118, (including speed and heading), measured acceleration 1120, and other outputs measurable by sensors of the AV 100.

In an embodiment, data about the disturbance 1110 is detected in advance, e.g., by a sensor such as a camera or LiDAR sensor, and provided to a predictive feedback module 1122. The predictive feedback module 1122 then provides data to the controller 1102 that the controller 1102 can use to adjust accordingly. For example, if the sensors of the AV 100 detect ("see") a hill, this data can be used by the controller 1102 to prepare to engage the throttle at the appropriate time to avoid significant deceleration.

Block Diagram of the Inputs, Outputs, and Components of the Controller

Figure 12:
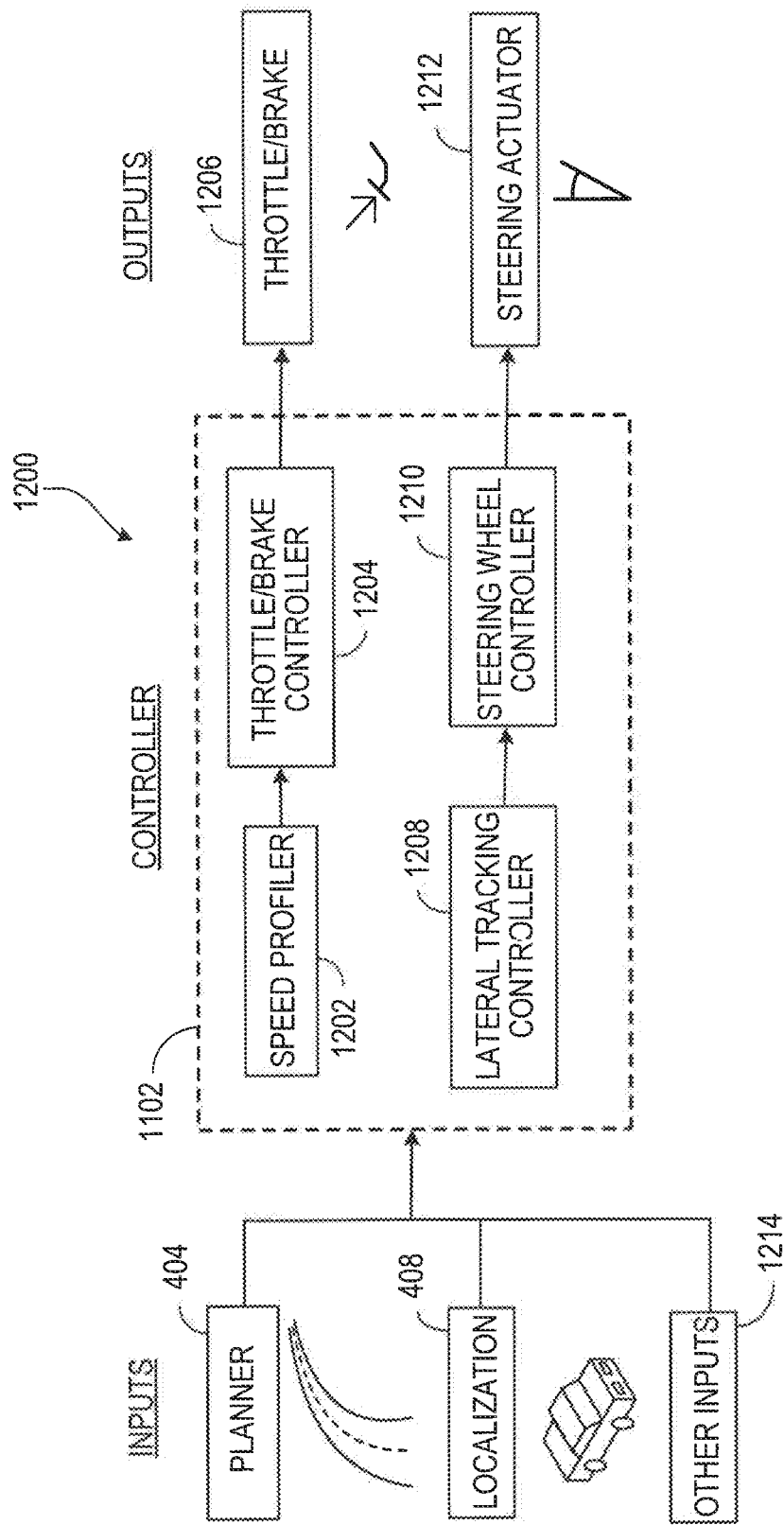
FIG. 12 illustrates a block diagram of the inputs, outputs, and components of a controller, in accordance with one or more embodiments.

FIG. 12 illustrates a block diagram 1200 of the inputs, outputs, and components of the controller 1102. The controller 1102 has a speed profiler 1202 which affects the operation of a throttle/brake controller 1204. For example, the speed profiler 1202 instructs the throttle/brake controller 1204 to engage acceleration or engage deceleration using the throttle/brake 1206 depending on, e.g., feedback received by the controller 1102 and processed by the speed profiler 1202.

The controller 1102 also has a lateral tracking controller 1208 which affects the operation of a steering controller 1210. For example, the lateral tracking controller 1208 instructs the steering controller 1204 to adjust the position of the steering angle actuator 1212 depending on, e.g., feedback received by the controller 1102 and processed by the lateral tracking controller 1208.

The controller 1102 receives several inputs used to determine how to control the throttle/brake 1206 and steering angle actuator 1212. A planning module 404 provides data used by the controller 1102, for example, to choose a heading when the AV 100 begins operation and to determine which road segment to traverse when the AV 100 reaches an intersection. A localization module 408 provides data to the controller 1102 describing the current location of the AV 100, for example, so that the controller 1102 can determine if the AV 100 is at a location expected based on the manner in which the throttle/brake 1206 and steering angle actuator 1212 are being controlled. In an embodiment, the controller 1102 receives data from other inputs 1214, e.g., data received from databases, computer networks, etc.

Figure 13:
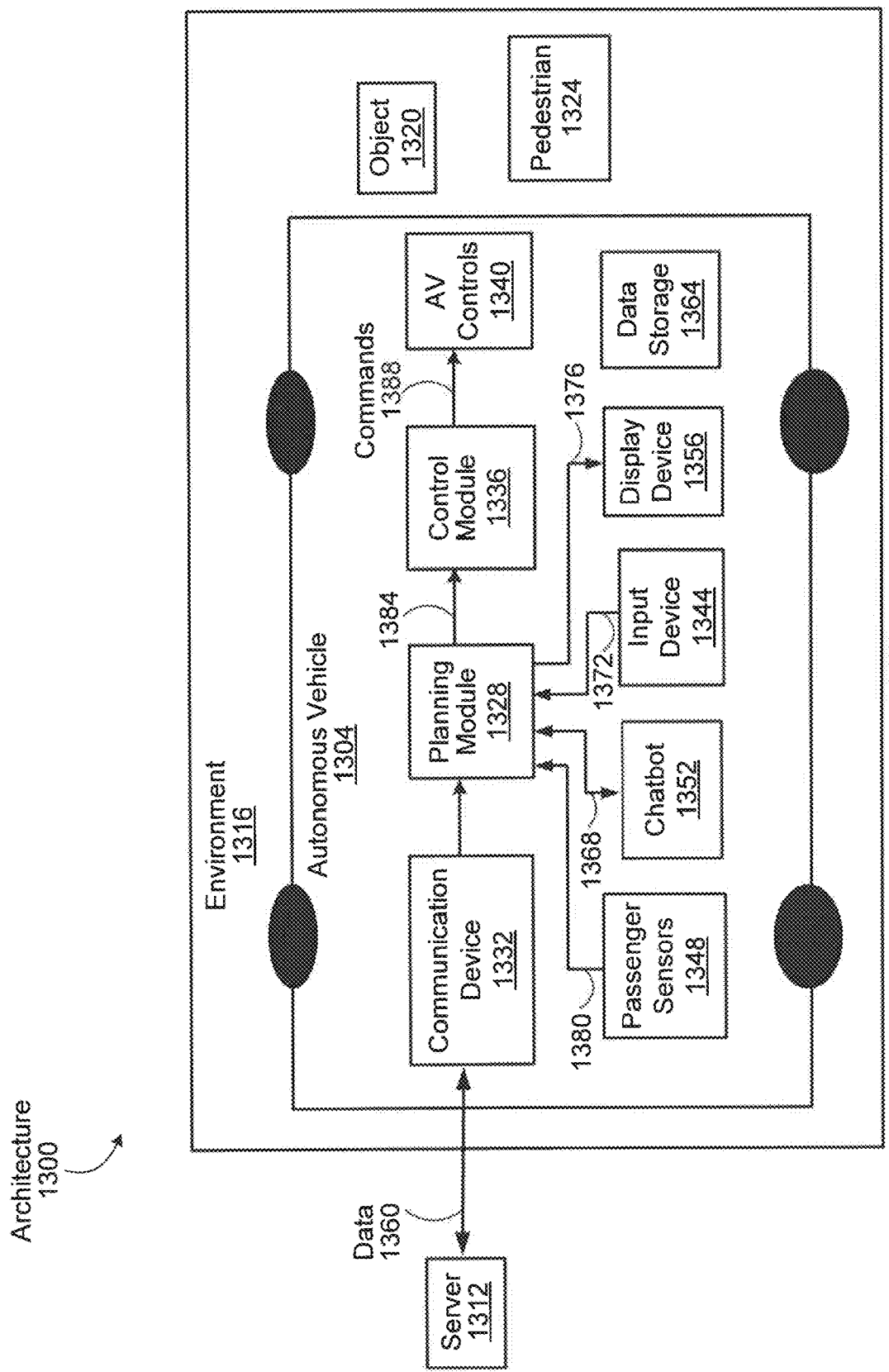
FIG. 13 illustrates a block diagram of an architecture for measuring and increasing passenger comfort during the operation of a vehicle, in accordance with one or more embodiments.

Architecture for Measuring and Increasing Passenger Comfort During Operation of a Vehicle FIG. 13 illustrates a block diagram of an architecture 1300 for measuring and increasing passenger comfort during the operation of an AV 1304, in accordance with one or more embodiments. The architecture 1300 includes a remote server 1312 and an environment 1316 surrounding the AV 1304. The server 1312 may be an embodiment of the server 136 shown in FIG. 1 and the AV 1304 may be an embodiment of the AV 100 shown in FIG. 1.

Referring to FIG. 13, the AV 1304 navigates autonomously or semi-autonomously along a trajectory through the environment 1316. The environment 1304 may be an embodiment of the environment illustrated and described above in detail with reference to FIG. 1. The environment 1316 represents a geographical area, such as a town, a neighborhood, or a road segment. In one embodiment, spatiotemporal locations within the environment 1316 are represented on an annotated map of the environment 1316. These spatiotemporal locations are used to generate a trajectory for the AV 1304. The environment 1316 contains the AV 1304, object 1320, and pedestrian 1324. In other embodiments, the architecture 1300 includes additional or fewer components than those described herein. Similarly, the functions can be distributed among the components and/or different entities in a different manner than is described here.

The server 1312 is communicatively coupled to the AV 1304 and transmits data to the AV 1304. In one embodiment, the server 1312 may be a "cloud" server as described in more detail above with reference to server 136 in FIGS. 1 and 2. Portions of the server 1312 may be implemented in software or hardware. For example, the server 1312 or a portion of the server 1308 may be part of a PC, a tablet PC, an STB, a smartphone, an internet of things (IoT) appliance, or any machine capable of executing instructions that specify actions to be taken by that machine.

The server 1312 stores data 1360 representing vehicle operation profiles for the AV 1304. The data 1360 representing vehicle operation profiles may be organized as a database or table of vehicle operation profiles stored on one or more of removable or non-removable memory devices, tape cassettes, zip cassettes, and computer hard drives. In one embodiment, a vehicle operation profile includes multiple data fields, each describing one or more parameters of the vehicle operation profile. In one example, a vehicle operation profile includes parameters such as a maximum operational speed, a maximum amplitude of fluctuation of acceleration, a maximum longitudinal acceleration, a maximum lateral acceleration, a maximum change in steering angle, a maximum rate of turn, or a maximum limit on a magnitude of jerk for the AV 1304.

In one embodiment, the maximum operational speed represents a predetermined speed limit (e.g., 40 mph), which is greater than, less than, or equal to the maximum legal speed limit. In another embodiment, the maximum operational speed is an offset from the legal speed limit of the road. For example, a passenger may prefer that the AV 1304 never exceed a limit of 10 mph below the legal speed limit of the road. In another embodiment, a vehicle operation profile specifies that the AV 1304 should never exceed a maximum acceleration or deceleration so that the passenger does not experience passenger discomfort. For example, the AV 1304 is configured to not accelerate more than N m/s/s or alter the AV's speed from 0-M mph in P seconds. In another embodiment, a vehicle operation profile specifies that the AV 1304 should never exceed a maximum longitudinal acceleration, i.e., acceleration in a straight line, with a positive value to indicate acceleration and a negative value for braking. In another example, a vehicle operation profile specifies that the AV 1304 should never exceed a maximum amplitude of fluctuation of acceleration or deceleration, thereby leading to a smoother acceleration or deceleration profile, e.g., a maximum of 3 m/s$^2$.

In one embodiment, a vehicle operation profile specifies that the AV 1304 should never exceed a maximum lateral acceleration, i.e., the force that is felt by the passenger as the AV 1304 executes a turn. Lateral acceleration is experienced in two dimensional space rather than one dimension, and may be represented as a velocity squared, divided by a radius of a circle. The maximum lateral acceleration in the vehicle operation profile is expressed in units of multiples of the earth's gravitational force or "g force." In an embodiment, a vehicle operation profile specifies that the AV 1304 should never exceed a maximum change in steering angle of the steering mechanism or a maximum rate of turning of the steering mechanism. The maximum limits on steering changes are expressed in degrees. The maximum limits ensure that the AV 13404 avoids swerving and yawing. In an embodiment, a vehicle operation profile specifies that the AV 1304 should never exceed a maximum limit on a magnitude of jerk for the AV 1304. The magnitude of jerk is a rate of change of acceleration of the AV 1304, i.e., a time derivative of acceleration. The planning module 1328 adjusts the operation of the AV 1304 to reduce the magnitude of jerk to provide a more comfortable ride to the passengers within the AV 1304.

In one embodiment, a vehicle operation profile includes a lateral clearance of the AV 1304 from the object 1320 or a pedestrian 1324 located in the environment 1316 containing the AV 1314. Persons skilled in the art would appreciate that a larger lateral clearance between the AV 1304 and objects provides increased passenger comfort. In one embodiment, a vehicle operation profile indicates a drivable region associated with passenger comfort for the AV 1304 or a magnitude of spatial freedom for the AV 1304 to maneuver laterally. In another example, the vehicle operation profile is based on data representing physical barriers and road features (e.g., a parking lot, a bridge, a construction zone, a curb of a road, a boundary of a lane, an intersection, or a building) contained within a map of the environment 1316, data from distance sensors (e.g., 121-123 in FIG. 1) representing distances from and movement of objects external to the AV 1306, or data from the planning module 1328 and control module 1336 representing a vehicular maneuver that the AV 1306 is about to perform or is already performing. In another example, a vehicular operation profile imposes limits on maneuvering, including any one of a lane change, passing another vehicle, parallel parking, a two-point turn, a left turn, a right turn, navigating a traffic circle, moving over for an emergency vehicle, turning into a parking lot, or merging onto a highway.

In one embodiment, each parameter (e.g., a maximum speed limit) in a vehicle operation profile is represented using a range of values (e.g., 5 mph-50 mph), including a maximum speed limit that a passenger is comfortable with up to an absolute maximum limit. In certain situations, the AV 1304 may need to exceed a maximum speed limit that a passenger is comfortable with to avoid accident, while still observing the absolute maximum limit. In another embodiment, one or more vehicle operation profiles are stored on the AV 1304 in the data storage unit 1364. The data storage 1364 is an embodiment of the data storage 142 or memory 144 shown in FIG. 1 and includes one or more of removable or non-removable memory devices, tape cassettes, zip cassettes, and computer hard drives. The data storage 1364 includes multiple data fields, each describing one or more attributes of a vehicle operation profile.

The server 1312 also stores data 1360 representing passenger profiles for the AV 1304. The data 1360 representing a passenger profile for the AV 1304 may be organized as a database or table of passenger profiles stored on one or more of removable or non-removable memory cards, tape cassettes, zip cassettes, and computer hard drives. In one example, the data 1360 representing a passenger profile for the AV 1304 includes multiple data fields, each describing one or more parameters of the passenger profile. In one embodiment, each passenger profile includes a set of ranges of operational parameters for the vehicle according to a level of passenger comfort preferred by the passenger. In one example, a passenger profile includes a range of values for a speed, a longitudinal acceleration, an amplitude of fluctuation of acceleration, a lateral acceleration, a change in steering angle, a rate of turn of the AV 1304, or a magnitude of jerk for the vehicle that the passenger prefers.

In one embodiment, the data 1360 representing passenger profiles for the AV 1304 includes a set of ranges of operational parameters for the vehicle that a particular passenger is not comfortable with. In one example, the passenger profile includes a range of values for a speed, a longitudinal acceleration, etc., that lead to passenger discomfort. The AV 1304 is instructed by the control module 1336 not to operate in those ranges that lead to discomfort for the particular passenger.

In one embodiment, a passenger profile includes biometric data (e.g., the data 1380 from the passenger sensors 1348) for the passenger recorded on previous rides. The biometric data 1380 for each passenger includes biofeedback measurements and values derived from such measurements. In one example, the data 1360 representing a passenger profile includes the passenger's skin conductance, pulse, heart-rate, body temperature, facial expressions, magnitude of pupil dilation, or pressure exerted by the passenger on seat arm rests associated with a speed or a longitudinal acceleration of the AV 1304, etc. Passenger biometric data is described in more detail below with reference to the passenger sensors 1348.

The stored biometric data is used to determine and be associated with a level of passenger comfort associated with particular operating characteristic of the AV 1304 (e.g., a speed of the AV 1304, a longitudinal acceleration of the AV 1304, etc.,). In one example, the level of passenger comfort is expressed on a scale of 1-10, with 1 representing the least comfortable setting for the operating characteristic and 10 representing the most comfortable setting for the operating characteristic. A maximum speed for the AV 1304 of 65 mph may be associated with a passenger comfort level of 5 while a maximum speed for the AV 1304 of 55 mph may be associated with a passenger comfort level of 9. In another example, a stored vehicle operation profile associated with a level of passenger comfort that is below a threshold T (e.g., 4-5) is deleted by the server 1312 or planning module 1328. This prevents stored vehicle operation profiles associated with lower levels of passenger comfort from being transmitted by the server 1312 for use by the AV 1304.

In one embodiment, passenger comfort data and vehicle operational parameters stored in a passenger profile are associated with temporal data including a time of day, a day of week, a geographical location, or a weather pattern. The temporal data is matched to the passenger comfort data, such that the planning module 1328 can match the AV 1304's driving characteristics to the temporal data. For example, a particular passenger may prefer driving faster on Monday mornings while riding to work than on Saturday afternoons while sightseeing on vacation. Another passenger may experience discomfort driving above a certain speed in the rain even though the AV 1304 is able to drive and maneuver safely in the rain at that speed. Similarly, the passenger may prefer to drive slowly within a certain geographical location in order to look at the buildings more closely if the passenger has not visited the location before.

In one embodiment, a stored passenger profile includes demographic data of the passenger including the passenger's age, address, gender, state or city of residence, occupation or income, or education. The demographic data is associated with vehicle operating metrics (e.g., a maximum speed, a maximum acceleration, etc.,) that the passenger is comfortable with. In one embodiment, the demographic data for a passenger is compared to demographic data for other passengers to match passengers for car-pooling so that the AV 1304 operates using a common vehicle operation profile that is optimally comfortable for all the passengers in the car-pool. In another example, the AV 1304 operates using a vehicle operation profile that is associated with a particular passenger (who is not riding in the AV 1304) who is demographically similar to a new passenger riding in the AV 1304.

In one embodiment, the server 1312 also stores data 1360 representing ride pricing incentives to be transmitted to a passenger riding in the AV 1304. The ride pricing incentives incentivize the passenger to allow biometric data collection within the AV 1304. The ride pricing incentives provide a cheaper ride to the passenger as well as allow the AV 1304 to use the biometric data collection to adjust the AV 104's vehicle operation profile to increase the passenger's comfort level. For example, the ride pricing incentives may provide a free ride to the passenger after 9 paid rides if the passenger allows biometric data collection within the AV 1304. In another example, the ride pricing incentives are associated with a demographic data or profile of the passenger.

In one embodiment, a stored passenger profile also stores data 1360 representing a preferred or maximum drive aggressiveness metric. A drive aggressiveness metric is an aggregate value (e.g., weighted average) of the parameters (e.g., maximum speed, maximum acceleration, etc.,) in a vehicle operation profile. The drive aggressiveness metric represents a degree of aggressiveness in driving. In one example, the drive aggressiveness metric is represented by set of functions $\{f1(p1, p2, \ldots, pn), (f2(p7, p9), \ldots\}$, where f1 and f2 are functions of the parameters in a vehicle operation profile and p1, p2, . . . , pn are the parameters of the vehicle operation profile. The drive aggressiveness metric is used to define or tune the vehicle operation profile for a passenger or a trip. For example, an older passenger may prefer a lower drive aggressiveness metric than a younger passenger.

In one embodiment, one or more passenger profiles, ride pricing incentives, or drive aggressiveness metrics are stored on the AV 1304 itself (e.g., in the data storage 1364). In one example, the data storage 1364 includes multiple data fields, each describing one or more attributes of a passenger profile, ride pricing incentives, or drive aggressiveness metrics.

The object 1320 is a physical object external to the AV 1304. For example, the object 1320 may be an environmental feature such as a construction zone, a building, a traffic sign, a physical curb of a road, or a marking on a lane boundary, etc. The object 1320 may be another vehicle, a cyclist, or a pedestrian. In one embodiment, the object 1320 and the pedestrian 1324 are classified by the AV 1304 (e.g., grouped into types such as pedestrian, automobile, etc.,) and data representing the classified object 1320 and pedestrian 1324 is provided to the planning module 1328 of the AV 1304 to generate a trajectory for the AV 1304. Objects that are external to the AV 1304 are described in more detail above with reference to objects 416 in FIGS. 4 and 5.

The AV 1304 includes a communication device 1332, the planning module 1328, a control module 1336, AV controls 1340 (e.g., steering, brakes, throttle), an input device 1344, one or more passenger sensors 1348, a chatbot 1352, a display device 1356, and the data storage 1364. The communication device 1332 may be an embodiment of the communication device 140 shown in FIG. 1, the planning module 1328 may be an embodiment of the planning module 404 shown in FIG. 4, the control module 1336 may be an embodiment of the control module 106 shown in FIG. 1, the AV controls 1340 may be an embodiment of the controls 420*a-c* shown in FIG. 4, the input device 1344 may be an embodiment of the input device 314 shown in FIG. 3, and the display device 1356 may be an embodiment of the display 312 shown in FIG. 3. In other embodiments, the AV 1304 includes additional or fewer components than those described herein. Similarly, the functions can be distributed among the components and/or different entities in a different manner than is described here.

The communication device 1332 communicates data 1360 (e.g., a vehicle operation profile, a passenger profile, ride pricing incentives, or drive aggressiveness metrics) with the server 1312, the planning module 1328, a passenger within the AV 1304, or other vehicles. The communication device 1332 is communicatively coupled to the server 1312 across a network. In an embodiment, the communication device 1332 communicates across the Internet, an electromagnetic spectrum (including radio and optical communications), or other media (e.g., air and acoustic media). Portions of the communication device 1332 may be implemented in software or hardware. In one example, the communication device 1332 or a portion of the communication device 1332 is part of a PC, a tablet PC, an STB, a smartphone, an internet of things (IoT) appliance, or any machine capable of executing instructions that specify actions to be taken by that machine. The communication device 1332 is described in more detail above with reference to communication device 140 in FIG. 1.

The one or more passenger sensors 1348 measure passenger comfort data 1380 of a passenger riding in the AV 1304. The passenger comfort data 1380 represents a level of passenger comfort experienced during a ride with respect to the vehicle operation profile. The passenger comfort data 1380 is used to determine how comfortable the passenger is and adjust the vehicle operation profile 1384 to increase the level of passenger comfort experienced during the ride. The passenger comfort data 1380 is based on measuring various metrics, for example, eyes-open metrics or eyes-closed metrics. Eyes-open metrics are measured by the passenger sensors 1348 based on a passenger's visual experience of the environment 1316 when the passenger is riding in the AV 1304. For example, eyes-open metrics include the AV's distance from environmental features (curbs, construction zones, lane barriers, buildings, etc.,), the AV's distance from other vehicles or pedestrians, or the passenger's view of the road. Eyes-closed metrics are measured by the passenger sensors 1348 based on a passenger's non-visual experience when the passenger is riding in the AV 1304. For example, eyes-closed metrics include velocity, acceleration, lateral acceleration, degree of steering angle, etc.

In one embodiment, the passenger sensors 1348 include biometric sensors used to measure distinctive, measurable physiological characteristics of the passenger representing a comfort level. For example, the passenger sensors 1348 include an electrodermal sensor, a pulse and heart rate monitor, a sphygmomanometer (blood pressure monitor), or a body temperature sensor (e.g., Infrared thermometer). The passenger comfort data 1380 includes biometric data such as electrodermal activity, a pulse, a heart-rate, blood pressure, or a body temperature. The electrodermal activity of the passenger causes variation in the electrical characteristics of the skin and is also known as skin conductance, galvanic skin response, or electrodermal response. The electrodermal activity, pulse, heart rate, blood pressure, and temperature of the passenger is a measure of emotional and sympathetic responses and is used to determine passenger comfort. In an embodiment, the passenger sensors 1348 include sensors for measuring physical characteristics of the passengers. For example, the passenger sensors 1348 may include a weighing scale to measure the passenger's weight and a laser scanner or an internal camera to measure the passenger's height.

In one embodiment, the passenger sensors 1348 include one or more imaging sensors used to record images of a passenger representing a comfort level. For example, the passenger sensors 1348 include a camera, a webcam, or an eye scanner. The passenger comfort data 1380 includes imaging data such as facial expressions or a pupillary response (e.g., constriction response or magnitude of pupil dilation). The magnitude of pupil dilation varies the size of the pupil via the optic and oculomotor cranial nerve representing an amount of adrenaline, and is used to determine passenger comfort.

In one embodiment, the passenger sensors 1348 include one or more pressure sensors on the seat, weight sensors embedded on the AV's floor below a passenger's feet, or a wearable glove including haptic sensors used to record the passenger comfort data 1380, such as a pressure exerted by a passenger on seat arm rests, seat back, or a clenched fist. For example, the passenger sensors 1348 include a strain gauge to detect strain due to applied pressure, a capacitive diaphragm, or an electromagnetic sensor to measure change in inductance due to pressure. A magnitude of pressure or haptic feedback exerted by the passenger on the seat arm rests, seat back, or floor represents a level of passenger discomfort associated with the vehicle operation profile.

In one embodiment, the passenger comfort data 1380 is measured relative to an operating speed of the AV 1304. In this embodiment, different levels of passenger comfort (e.g., 5-9) are associated with different operating speeds (e.g., 30 mph-60 mph) and are used to tune the vehicle operation profile or be stored in the passenger profile for future use.

The chatbot 1352 is a computer program or an artificial intelligence that conducts a conversation via auditory or textual methods with a passenger. The chatbot 1352 is designed to simulate how a human driver would behave as a conversational partner, thereby passing the Turing test. In one embodiment, the chatbot 1352 uses a natural language processing system or scans for keywords within input 1368 from the passenger and then determines a reply from a database. The chatbot 1352 is communicatively coupled to the planning module 1328. The planning module 1328 transmits data 1368 representing the vehicle operation profile to the chatbot 1352 and receives data representing a level of comfort from the passenger. In one embodiment, the chatbot 1352 is used to express the passenger's preference for a particular vehicle operation profile, a particular drive aggressiveness metric, or a desire by the passenger for the AV 1304 to speed up or accelerate more slowly. In another embodiment, the AV 1304 integrates voice capture and recognition devices with the chatbot 1352 to analyze a pitch of voice of the passenger. The pitch of the passenger's voice represents a level of comfort experienced during the ride.

The input device 1344 receives data 1372 from a passenger within the AV 1304. In one embodiment, the data 1372 represents instructions for driving, a preference for a vehicle operation profile, or a desired drive aggressiveness metric. The input device 1344 transmits the data 1372 to the planning module 1328. In one embodiment, the input device 1344 translates data 1372 from a human-readable format or natural language to a computer program, pseudocode, machine-language format, or assembly-level format for the planning module 1328 to use. In one embodiment, the input device 1344 is integrated with or coupled to the chatbot 1352. The input device 1344 may include a touchscreen display or keyboard. The input device 1344 is described in more detail above with reference to the input device 314 and cursor controller 316 in FIG. 3.

In one embodiment, the AV 1304 further includes a perception module to identify the objects 1320 or 1324 and transmit data representing the identified objects to the planning module 1328. In one embodiment, the perception module 1348 includes a camera or a LiDAR to determine a distance from the objects 1320 or 1324. The perception module 1348 is described in more detail above with reference to the perception module 402 in FIG. 4.

The display device 1356 provides data 1376 to the passenger riding in the AV 1304. In one embodiment, the data 1376 represents ride pricing incentives to incentivize the passenger to allow biometric data collection within the AV 1304. In another embodiment, the data 1376 represents the current vehicle operation profile or drive aggressiveness metric of the AV 1304. In another embodiment, the data 1376 represents a range of vehicle operation profiles or drive aggressiveness metrics of the AV 1304 that the passenger may select from.

The planning module 1328 determines the vehicle operation profile for the AV 1304 and updates the vehicle operation profile based on the measured passenger comfort data 1380. The planning module 1328 is communicatively coupled to the communication device 1332 to receive instructions or data representing a vehicle operation profile, a stored passenger profile, a drive aggressiveness metric, or ride pricing incentives from the server 1312. The planning module 1328 is communicatively coupled to the passenger sensors 1348 to receive the passenger comfort data 1380. The planning module 1328 is communicatively coupled to the chatbot 1352 to receive data 1368 representing communication from the passenger. The planning module 1328 is communicatively coupled to the input device 1344 to receive data 1372 representing passenger preferences. The planning module 1328 is communicatively coupled to the display device 1356 to transmit data 1376 representing ride pricing incentives or drive aggressiveness options. In one embodiment, portions of the planning module 1328 are implemented in software or hardware. For example, the planning module 1328 or a portion of the planning module 1328 may be part of a PC, a tablet PC, an STB, a smartphone, an internet of things (IoT) appliance, or any machine capable of executing instructions that specify actions to be taken by that machine. The planning module 1328 is described in more detail above with reference to planning module 404 in FIG. 4.

The planning module 1328 determines the vehicle operation profile for the AV 1304. In one embodiment, the planning module receives data 1360 from the server 1312 representing a vehicle operation profile to be used. In another embodiment, the vehicle operation profile is partially determined based on data 1360 representing a stored passenger profile (e.g., stored on the server 1312) of a passenger riding in the AV 1304. In one embodiment, the vehicle operation profile is determined based on values of parameters (e.g., a maximum speed, a maximum acceleration, e.g.,) associated with the stored passenger profile. Once the passenger enters the AV 1304 to begin a ride, the planning module 1328 adjusts the vehicle operation profile to match the parameters in the passenger profile.

In one embodiment, determining a vehicle operation profile for a new passenger includes aggregating a plurality of stored vehicle operation profiles associated with other passengers (not presently riding in the AV 1304). The stored passenger profiles of the other passengers are demographically similar to a passenger profile of the new passenger. For example, when a 50-year-old passenger enters the AV 1304, the planning module 1328 may determine the vehicle operation profile by aggregating a plurality of stored vehicle operation profiles associated with other passengers who are between 48 and 52 years old. Although the other passengers are not riding in the AV 1304 at present, they likely have similar preferences for drive aggressiveness metrics or vehicle operational parameters.

In one embodiment, the vehicle operation profile is determined based on data (e.g., 1372) received, using the input device 1344, from the passenger. For example, a particular passenger may specify that the AV 1304 operate 10 mph below the legal speed limit. In another embodiment, the planning module 1328 transmits data 1368 representing a current vehicle operation profile to a passenger via the chatbot 1352 and receives, using the chatbot 1352, data representing a passenger preference from the passenger. In one example, the planning module 1328 receives data 1368 representing a level of passenger comfort from the chatbot 1352 by analyzing language patterns or text of the passenger's responses to determine the level of passenger comfort.

The planning module 1328 updates the vehicle operation profile based on the received passenger comfort data 1380. The updated vehicle operation profile represents and is used to provide a more comfortable ride to the passenger. In one embodiment, the AV 1304's vehicle operation profile and passenger comfort data 1380 are treated as a controlled system. The input to the system includes the vehicle operation profile, while the system's status (level of passenger comfort) is measured by the sensors 1348. An error signal is determined as a departure of the level of passenger comfort from an optimal passenger comfort level. The determined error is interpreted by the planning module 1348 to adjust the vehicle operation profile, commanding the AV controls 1340 to adjust the AV 1304 operation. The resulting change in vehicle operation profile reduces the error, thereby increasing the passenger comfort.

In one embodiment, the planning module 1328 updates the vehicle operation profile by determining an aggregate passenger comfort metric based on passenger comfort data 1380 of a plurality of passengers in the AV 1304. The aggregate passenger comfort metric represents an overall or average level of passenger comfort of the plurality of passengers and is used when more than one passenger is riding. The planning module 1328 adjusts the vehicle operation profile 1384 based on the aggregate passenger comfort metric.

In one embodiment, the planning module 1328 updates the vehicle operation profile 1384 by determining a desired drive aggressiveness metric based on aggregated passenger comfort data 1380 of a plurality of passengers in the AV 1304. The drive aggressiveness metric, as described above, is an aggregate metric representing a degree of aggressiveness of vehicle operation. The planning module 1328 adjusts the vehicle operation profile 1384 based on the desired drive aggressiveness metric. In one embodiment, if a drive aggressiveness metric based on aggregated passenger comfort data 1380 of a plurality of passengers reveals that the AV 1304 is driving too aggressively, the vehicle operation profile is adjusted to be less aggressive. In another embodiment, a particular passenger specifies to a ride-hailing application for the AV 1304 that the passenger wishes to share a ride with only other passengers whose stored passenger profiles are associated with a particular vehicle operation profile or drive aggressiveness metric. In this embodiment, the preference expressed by the particular passenger is used to determine which of several AVs to summon or how to route AVs in a car-pool to pick up the selected passengers.

In one embodiment, the updating of the vehicle operation profile is based on a weighted aggregate of passenger comfort data 1380 of a plurality of passengers in the AV 1304. Several passengers may be riding in the AV 1304. The passenger comfort data 1380 of a higher-priority passenger is weighted higher than passenger comfort data 1380 of a lower-priority passenger. In one embodiment, although the passenger comfort data 1380 of a younger passenger indicates that the ride is comfortable, the passenger comfort data 1380 of an older passenger indicates that the ride is uncomfortable. The vehicle operation profile will therefore be updated to reduce drive aggressiveness. In another embodiment, the vehicle operation profile is updated such that a level of comfort for the most uncomfortable passenger is reduced.

In one embodiment, the planning module 1328 uses a machine learning model to receive the passenger comfort data 1380 and update the vehicle operation profile 1384 based on the passenger comfort data 1380. The planning module 1328 extracts features from training sets of the passenger comfort data 1380. The features are used for training the machine learning model based on training labels. In one embodiment, the machine learning model is configured to determine a score based on the passenger comfort data 1380, wherein the score is indicative of a level of passenger comfort.

In one embodiment, the planning module 1328 applies machine learning techniques to train the machine learning model that when applied to passenger comfort data 1380 outputs indications of whether the passenger comfort data 1380 has a particular associated property or properties, e.g., that when applied to features of received passenger comfort data 1380 outputs estimates of whether the passenger is experiencing a comfortable ride. In other embodiments, different machine learning techniques, such as linear support vector machine (linear SVM), boosting for other algorithms (e.g., AdaBoost), logistic regression, naïve Bayes, memory-based learning, random forests, bagged trees, decision trees, boosted trees, or boosted stumps, are used.

In some embodiment embodiments, a validation set is formed of additional features, other than those in the training sets, which have already been determined to have or to lack the property in question. The planning module 1328 applies the trained machine learning model to the features of the validation set to quantify the accuracy of the machine learning model. Common metrics applied in accuracy measurement include: Precision=TP/(TP+FP) and Recall=TP/(TP+FN), where precision is how many the machine learning model correctly predicted (TP or true positives) out of the total it predicted (TP+FP or false positives), and recall is how many the machine learning model correctly predicted (TP) out of the total number of features that did have the property in question (TP+FN or false negatives). The F score (F-score=2×PR/(P+R)) unifies precision and recall into a single measure. In one embodiment, the planning module 1328 iteratively re-trains the machine learning model until the occurrence of a stopping condition, such as the accuracy measurement indication that the machine learning model is sufficiently accurate, or a number of training rounds having taken place. The trained machine learning model receives real-time passenger comfort data 1380 and transmits an updated vehicle operation profile 1384 to the control module 1336.

In one embodiment, the planning module 1328 determines or adjusts a trajectory (e.g., 414 in FIG. 4) of the AV 1304 based on the passenger comfort data 1380 or data 1360 received from a stored passenger profile of a passenger. The planning module 1328 uses a directed graph representation of the road network to generate the trajectory including a plurality of travel segments. Each travel segment (e.g., edge 1010a in FIG. 10) represents a portion of the trajectory 414. Each travel segment in the trajectory is associated with a level of passenger comfort (e.g., stored from previous rides). The planning module 1328 evaluates the cost (in terms of passenger discomfort) of navigating the AV 1304 along a particular trajectory. The planning module 1328 determines or adjusts the trajectory for the AV 1304 by optimizing the level of passenger comfort across the plurality of travel segments.

In an alternative embodiment, the planning module 1328 receives, using the input device 1344, data 1372 from a passenger representing a preferred drive aggressiveness metric. The planning module 1328 adjusts the vehicle operation profile based on the preferred drive aggressiveness metric. In this embodiment, the drive aggressiveness metric and passenger preference is independent of the measured passenger comfort data 1380. For example, although the passenger's heart is racing (as measured by sensors 1348), the passenger may prefer a more thrilling ride. In one embodiment, the planning module 1328 associates each stored vehicle operation profile of a plurality of stored vehicle operation profiles with a level of passenger comfort based on the passenger data 1380. In one embodiment, certain stored vehicle operation profiles are associated with a lower level of passenger comfort. The planning module 1328 deletes stored vehicle operation profiles associated with a level of passenger comfort below a threshold T.

The control module 1336 is communicatively coupled to the planning module 1328. The control module 1336 receives data 1384 representing an updated vehicle operation profile and the present AV position (e.g., 418 in FIG. 4), and operates the AV controls 1340 in a manner that will cause the AV 1304 to operate according to the updated vehicle operation profile 1384. The control module 1336 navigates the AV 1304 by issuing one or more of throttle, braking, and steering commands 1388 in accordance with the updated vehicle performance profile 1384. In one embodiment, portions of the control module 1336 are implemented in software or hardware. For example, the control module 1336 or a portion of the control module 1336 may be part of a PC, a tablet PC, an STB, a smartphone, an internet of things (IoT) appliance, or any machine capable of executing instructions that specify actions to be taken by that machine. The control module 1336 is described in more detail above with reference to control module 406 in FIGS. 4 and 11.

The AV controls 1340 receive the commands 1388 from the control module 1336 and adjust the steering, brakes, and throttle of the AV 1304. In one embodiment, portions of the AV controls 1340 are implemented in software or hardware. For example, the AV controls 1340 or a portion of the AV controls 1340 may be part of a PC, a tablet PC, an STB, a smartphone, an internet of things (IoT) appliance, or any machine capable of executing instructions that specify actions to be taken by that machine. The AV controls 1340 are described in more detail above with reference to modules 406 and 420*a-c* in FIG. 4.

The benefits and advantages of the embodiments disclosed herein are that the updated vehicle operation profile provides a more comfortable ride to the passenger or a plurality of passengers. By using the aggregate metrics for passenger comfort and drive aggressiveness disclosed herein, the AV 1304 ensures that passengers are not made comfortable at the expense of other passengers. The disclosed preferred drive aggressiveness metric can be used by a passenger to select a personal level of drive aggressiveness and comfort. While traditional route selection methods may attempt to increase a lateral distance from an obstacle when it is encountered, the embodiments disclosed herein increase the lateral clearance globally for all objects, thereby providing a more comfortable and more optimal trajectory.

Figure 14:
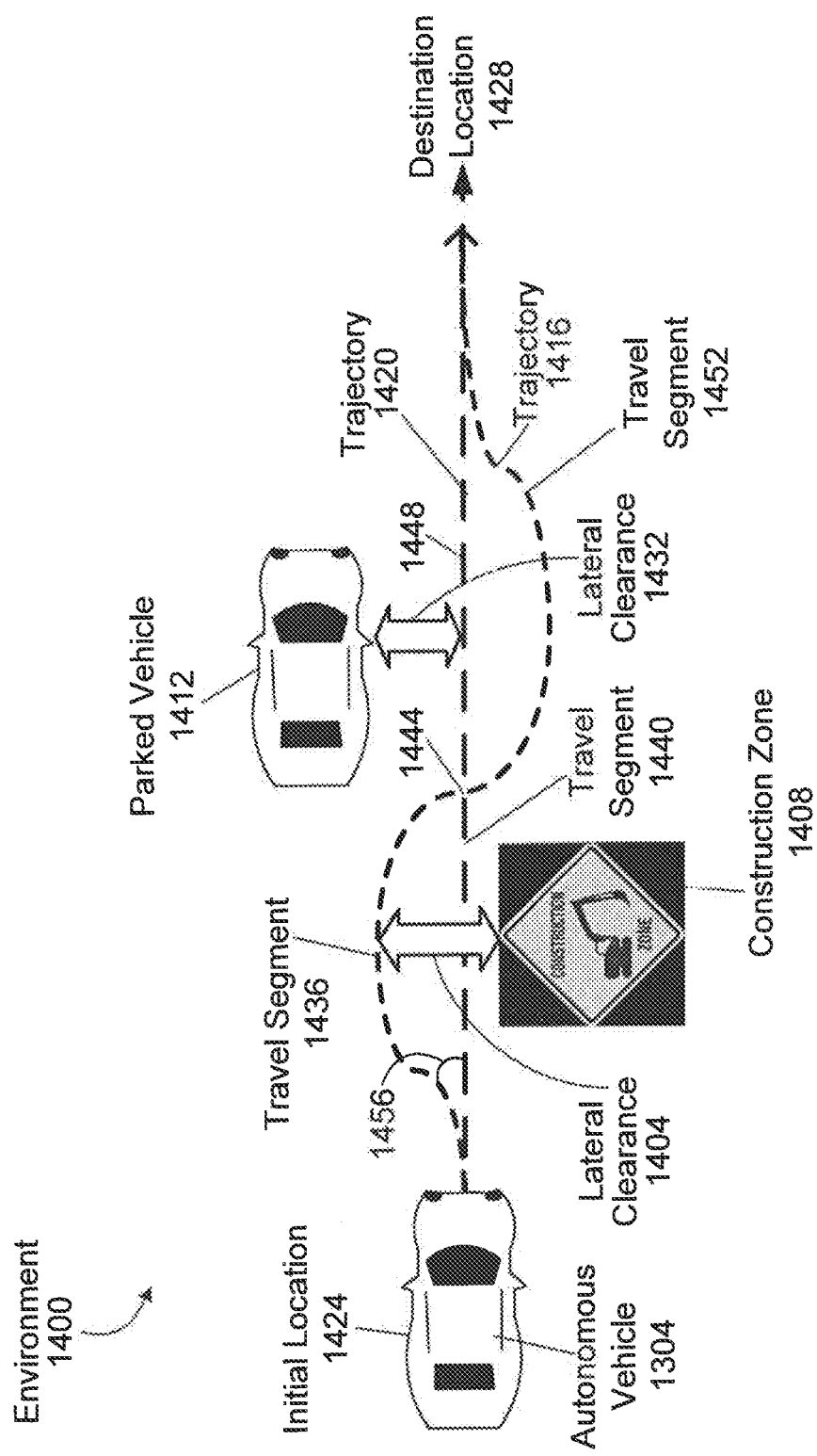
FIG. 14 illustrates an example of measuring and increasing passenger comfort during the operation of a vehicle, in accordance with one or more embodiments.

Example of Measuring and Increasing Passenger Comfort During Operation of a Vehicle FIG. 14 illustrates an example of measuring and increasing passenger comfort during the operation of the AV 1304, in accordance with one or more embodiments. The vehicle operation profile includes a lateral clearance of the AV 1304 from an object (e.g., 1412) or a pedestrian located in an environment 1400 containing the AV 1304. For example, a parameter of the vehicle operation profile represents a desired (or minimum limit on) lateral clearance from objects. The vehicle operation profile further includes a maximum limit on change of steering angle for the AV 1304 to provide a more comfortable ride.

In FIG. 14, the AV 1304 is initially located at spatiotemporal location 1424 and desires to travel to the destination spatiotemporal location 1428. There are two potential travel segments 1440 and 1436 between the initial spatiotemporal location 1424 and the intermediate spatiotemporal location 1444. The lateral clearance 1404 represents a distance between the travel segment 1438 and the construction zone 1408. The angle 1456 represents a change in steering angle between the travel segments 1440 and 1436. The lateral clearance 1404 is greater than the minimum limit on lateral clearance in the vehicle operation profile while the angle 1456 does not violate the maximum limit in the vehicle operation profile. Hence the AV 1304 selects travel segment 1436.

Once the AV 1304 is located at the intermediate spatiotemporal location 1444, there are two potential travel segments 1448 and 1452 between the intermediate spatiotemporal location 1444 and the destination spatiotemporal location 1428. The lateral clearance 1432 represents a distance between the travel segment 1448 and the parked vehicle 1412. The lateral clearance 1432 is greater than the minimum limit on lateral clearance in the vehicle operation profile. However, if the AV 1304 were to navigate on travel segment 1452, the change in steering angle would violate the maximum limit in the vehicle operation profile. Hence the AV 1304 selects travel segment 1448.

In one embodiment, the AV 1304 further tunes the trajectory based on a predictive passenger profile for a passenger. For example, if a passenger is older and data collected previously from older passengers indicates that such passengers prefer more leisurely, scenic routes to their destinations (e.g., 1436-1452) instead of using the shortest route (1440-1448), the AV plans a more leisurely, scenic route. While traditional route selection methods may attempt to increase a lateral distance from an obstacle when it is encountered, the embodiments disclosed herein increase the lateral clearance globally for all objects, thereby providing a more comfortable and more optimal trajectory.

Figure 15:
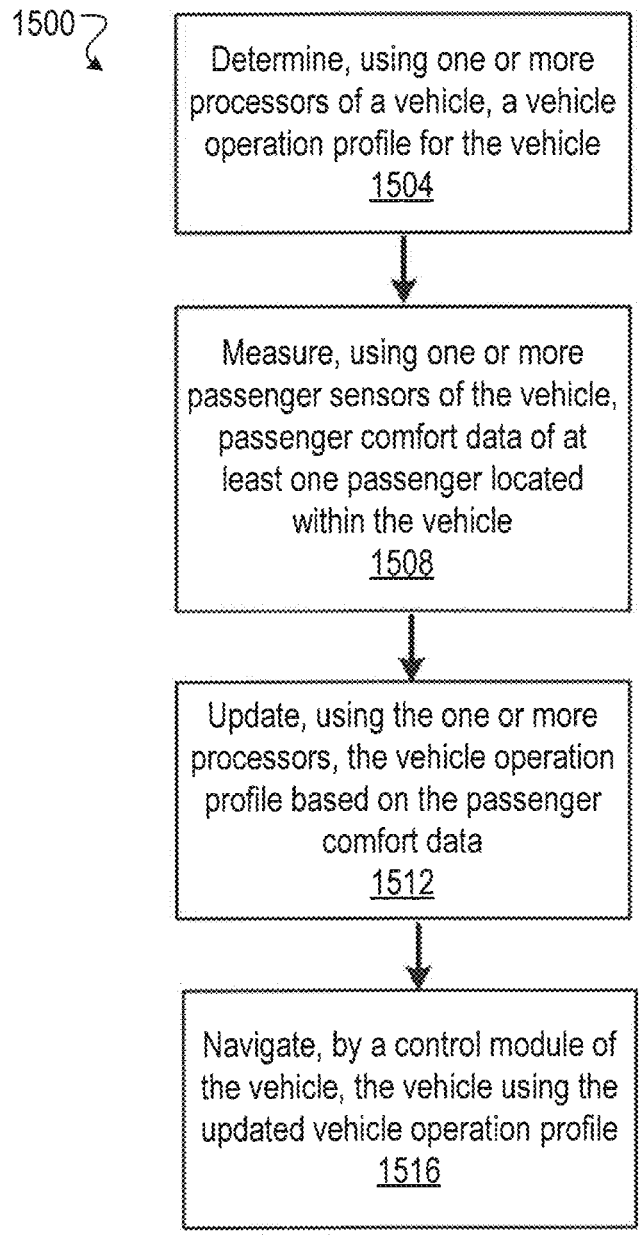
FIG. 15 illustrates a process for measuring and increasing passenger comfort during the operation of a vehicle, in accordance with one or more embodiments.

Process for Measuring and Increasing Passenger Comfort During Operation of a Vehicle FIG. 15 illustrates a process 1500 for measuring and increasing passenger comfort during the operation of the AV 1304, in accordance with one or more embodiments. In one embodiment, the process 1500 of FIG. 15 is performed by one or more components (e.g., the planning module 1328 in FIG. 13) of the AV 1304. Other entities (e.g., a remote server 1312 in FIG. 13) perform some or all of the steps of the process 1500 in other embodiments. Likewise, embodiments may include different and/or additional steps, or perform the steps in different orders.

The AV 1304 determines 1504 a vehicle operation profile for the AV 1304. In one embodiment, the planning module receives data (e.g., 1360 in FIG. 13) representing a vehicle operation profile to be used. In another embodiment, the vehicle operation profile is partially determined based on data 1360 received from a stored passenger profile (e.g., stored on the server 1312 in FIG. 13) of a passenger riding in the AV 1304. In one embodiment, the vehicle operation profile is determined based on values of parameters (e.g., a maximum speed, a maximum acceleration, etc.) associated with the stored passenger profile.

The AV 1304 measures 1508, using the one or more passenger sensors 1348, passenger comfort data (e.g., 1380 in FIG. 13) of a passenger located within the AV 1304. The passenger comfort data 1380 represents a level of passenger comfort experienced during a ride with respect to the vehicle operation profile. The passenger comfort data 1380 is used to determine how comfortable the passenger is and adjust the vehicle operation profile to increase the level of passenger comfort experienced during the ride. In one embodiment, the passenger sensors 1348 include biometric sensors used to measure distinctive, measurable physiological characteristics of the passenger representing a comfort level. In one embodiment, the passenger sensors 1348 include an electrodermal sensor, a pulse and heart rate monitor, a sphygmomanometer (blood pressure monitor), or a body temperature sensor (e.g., Infrared thermometer). The passenger comfort data 1380 includes biometric data such as electrodermal activity, a pulse, a heart-rate, blood pressure, or a body temperature. The electrodermal activity, pulse, heart rate, blood pressure, and temperature of the passenger is a measure of emotional and sympathetic responses and is used to determine passenger comfort.

The AV 1304 updates 1512 the vehicle operation profile based on the passenger data 1380. The updated vehicle operation profile (e.g., 1384 in FIG. 13) represents and is used to provide a more comfortable ride to the passenger. In one embodiment, the planning module 1328 updates the vehicle operation profile by determining an aggregate passenger comfort metric based on passenger comfort data 1380 of a plurality of passengers in the AV 1304. The aggregate passenger comfort metric represents an overall or average level of passenger comfort of all the passengers and is used when more than one passenger is riding. The planning module adjusts the vehicle operation profile 1384 based on the aggregate passenger comfort metric.

The AV 1304 navigates, using a control module (e.g., 1336 in FIG. 13), the AV 1304 using the updated vehicle operation profile 1384. The control module 1336 receives data 1384 representing the updated vehicle operation profile and the present AV position (e.g., 418 in FIG. 4), and operates the AV controls 1340 in a manner that will cause the AV 1304 to operate according to the updated vehicle operation profile 1384. The control module 1336 navigates the AV 1304 by issuing one or more of throttle, braking, and steering commands 1388 in accordance with the vehicle performance profile 1384.

Controlling Actuators Based on Load Characteristics

Figure 16:
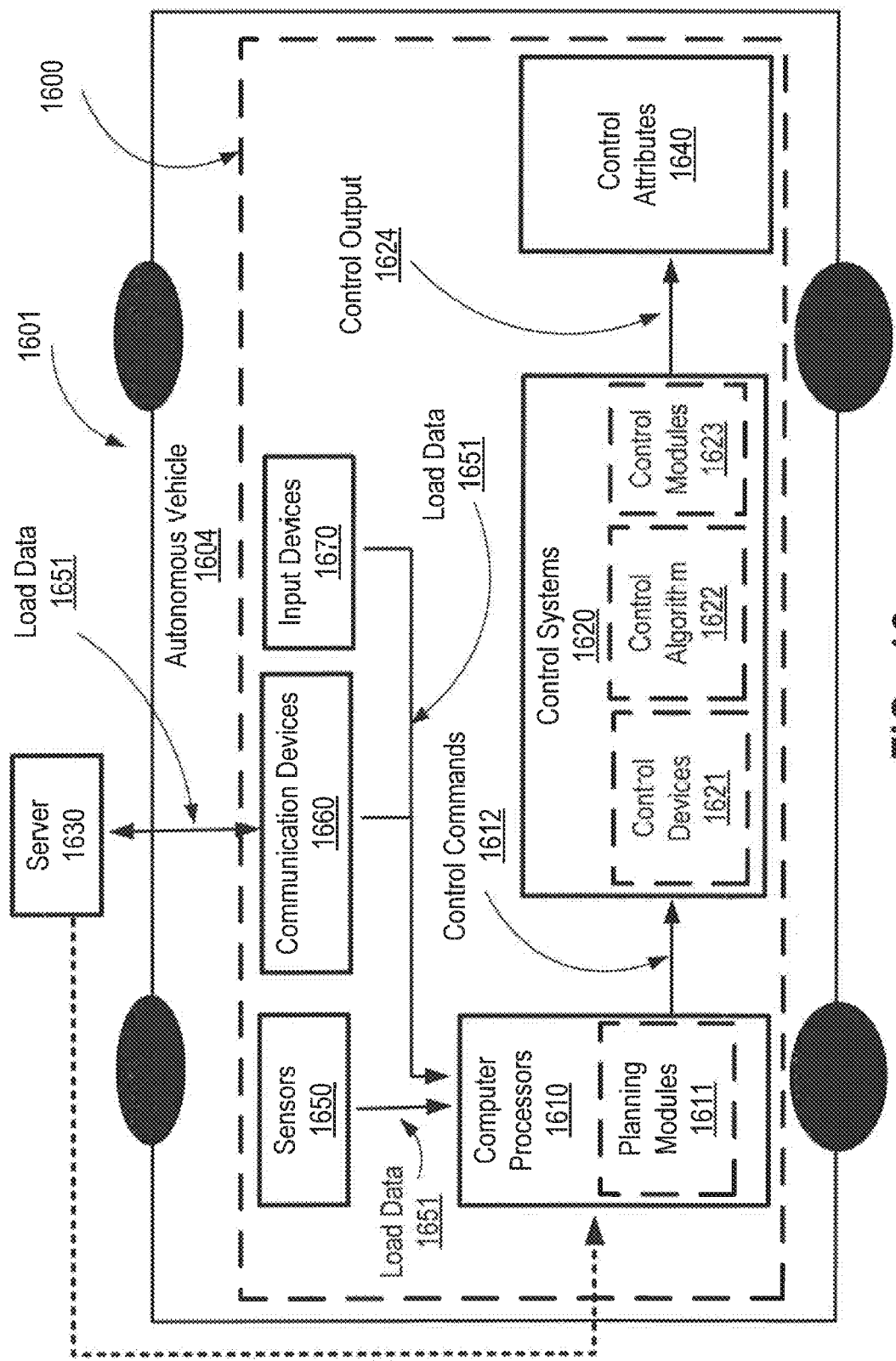
FIG. 16 illustrates an environment that includes an AV equipped with a system for controlling actuators based on load characteristics, in accordance with one or more embodiments.

FIG. 16 illustrates an environment 1601 that includes an AV 1604 equipped with a system 1600 for controlling actuators based on load characteristics according to at least one embodiment of the present disclosure. The AV 1604 may be substantially similar to AV 100 of FIG. 1. The AV 1604 may be fully autonomous or partially autonomous. The system 1600 includes computer processors 1610, control systems 1620, sensors 1650, communication devices 1660, and input devices 1670. Regarding the sensors 1650, communication devices 1660 and input devices 1670, the system 1600 may include all of these devices or just some of these devices. For example, in an embodiment, the system 1600 does not include the communication devices 1660. In an embodiment, the system 1600 does not include the input devices 1670. The sensors 1650 are configured to detect one or more load characteristics of the AV 1604. As described herein, a load characteristic refers to a characteristic of the passengers and/or cargo items aboard the AV 1604 or in an attached cargo vehicle. For example, a load characteristic may refer to the weight of one or more passengers and/or cargo items, the number of passengers and/or cargo items, the shape of one or more passengers and/or cargo items, the location within the AV 1604 of one or more passengers and/or cargo items, and so forth. In an embodiment, the sensors 1650 detect the weight of one or more passengers within the AV 1604. In an embodiment, the sensors 1650 detect the number of passengers inside the AV 1604. In an embodiment, the sensors 1650 detect the build/body shape of one or more passengers within the AV 1604. In an embodiment, the sensors 1650 detect various attributes, including weight, size, composition, etc., of one or more cargo items within or attached to the AV 1604. The sensors 1650 may also detect characteristics specifying the seating location of one or more passengers, characteristics specifying seatbelt usage information of one or more passengers, characteristics specifying one or more cargo object shapes, and so forth.

The sensors 1650 may include several sensors of different types that are configured to measure several different cargo attributes. In an embodiment, the sensors 1650 include one or more load sensors (i.e., strain gauge/load cell). In an embodiment, the sensors 1650 include light detection and ranging (LiDAR) devices. In an embodiment, the sensors 1650 include cameras. In an embodiment, the sensors 1650 include radio-frequency identification (RFID) readers, which can be either active, passive, or both. The sensors 1650 may also include capacitive sensors and inductive sensors. The sensors 1650 are located on or within several locations of the AV 1604. In an embodiment, one or more load sensors of the sensors 1650 are located within and/or beneath the seats of the AV 1604. One or more load sensors of the sensors 1650 may also be located within the seatbelt components associated with the passenger seats. In an embodiment, one or more load sensors, one or more inductive sensors, and/or one or more capacitive sensors are located on various locations of the AV 1604 suspension system (e.g., axel, springs, etc.). In an embodiment, one or more cameras, LiDARs and/or RFID readers are located inside the cabin of the AV 1604. In an embodiment, the AV 1604 is attached to a cargo vehicle (e.g., a towed vehicle, a trailer, etc.), using, for example, a hitch system. In an embodiment, one or more of the sensors 1650 are located on several locations of the hitch system. For example, one or more of the sensors 1650 may be placed on a trailer hitch, a ball mount, and/or a trailer ball when these components are used to attach a cargo vehicle to the AV 1604. One or more load sensors, one or more inductive sensors, and/or one or more capacitive sensors may also be located on various locations of the cargo vehicle's suspension system (e.g., axel, springs, etc.). Additionally, one or more cameras, LiDARs and/or RFID readers may be located within the cabin of the cargo vehicle.

The input devices 1670 are configured to receive load data 1651 from passengers within the AV 1604 or other personnel making use of the AV 1604, such as for object transportation purposes. For example, users of the AV 1604 may input load data 1651 representing the age of one or more passengers, the weight of one or more passengers, health information (e.g., illness, injury, pregnancy status, etc.) of one or more passengers, a number of cargo objects, the weight of one or more cargo objects, the shapes of one or more cargo objects, the position of one or more cargo objects, the fragility of one or more cargo objects, and so forth. The input devices 1670 transmit the load data 1651 to the computer processors 1610. The input devices 1670 may translate load data 1651 from a human-readable format or natural language to a computer program, pseudocode, machine-language format, or assembly-level format for the computer processors 1610 to use. The input devices 1670 include one input device or several input devices. The input devices 1670 may include a touch-screen display or keyboard. The input devices 1670 are described in more detail above with reference to the input device 314 and cursor controller 316 in FIG. 3.

The communication devices 1660 communicate load data 1651 to the server 1630, the computer processors 1610, a passenger within the AV 1604, or other vehicles. The communication devices 1660 may include one communication device or several communication devices. The communication devices 1660 are communicatively coupled to the server 1620 across a network. In an embodiment, the communication devices 1660 communicates across the Internet, an electromagnetic spectrum (including radio and optical communications), or other media (e.g., air and acoustic media). Portions of the communication devices 1660 may be implemented in software or hardware. For example, the communication device 1660 or a portion of the communication devices 1660 may be part of a PC, a tablet PC, an STB, a smartphone, an internet of things (IoT) appliance, or any machine capable of executing instructions that specify actions to be taken by that machine. The communication devices 1660 are described in more detail above with reference to the communication device 140 of FIG. 1.

The server 1630 is communicatively coupled to the computer processors 1630 and transmits load data 1651 to the computer processors 1610. In one embodiment, the server 1630 may be a "cloud" server as described in more detail above with reference to server 136 in FIGS. 1 and 2. Portions of the server 1630 may be implemented in software or hardware. For example, the server 1630 or a portion of the server 1630 may be part of a PC, a tablet PC, an STB, a smartphone, an internet of things (IoT) appliance, or any machine capable of executing instructions that specify actions to be taken by that machine.

The server 1630 stores load data 1651 representing one or more load characteristics of the AV 1604. The load data 1651 may be organized as a database or table of one or more load characteristics stored on one or more of removable or non-removable memory cards, tape cassettes, zip cassettes, and computer hard drives. In one embodiment, the load data 1651 may include multiple data fields, each describing one or more load characteristics. For example, the load data 1651 may include one or more load characteristics such as the age of one or more passengers, the weight of one or more passengers, health information (i.e., illness, injury, pregnancy status, etc.) of one or more passengers, a number of cargo objects, the weight of one or more cargo objects, the shapes of one or more cargo objects, the position of one or more cargo objects, and/or the fragility of one or more cargo objects. In an embodiment, the load characteristics of a passenger are associated with the passenger's customer profile. In an embodiment, the customer profile is used to match the passenger to vehicles by a ride hailing service.

The computer processors 1610 are configured to receive load data 1651 from the sensors 1650, the communication devices 1660, the server 1630, and/or the input devices 1670. As indicated previously, the load data represents one or more load characteristics. In an embodiment, the computer processors 1610 include only one computer processor. In an embodiment, the computer processors 1610 include more than one computer processor. The computer processors are further configured to algorithmically generate control commands 1612 based on the load data 1651. In an embodiment, the computer processors 1610 also generate control commands 1612 in accordance with other real-time sensor data and/or prior information. In an embodiment, the computer processors 1610 are substantially similar to the computer processors 146 referenced in FIG. 1.

In an embodiment, the computer processors 1610 are configured to determine a speed profile based on the load data 1651. As described herein, speed profile represents to the change in acceleration or jerk to cause the AV 1604 to transition from a first speed to at least a second speed. For example, a jagged speed profile describes rapid change in the speed of the AV 1604 via acceleration or deceleration. An AV 1604 with a jagged speed profile transitions between speeds quickly and therefore, may cause a passenger to experience an unpleasant/uncomfortable amount of force due to the rapid acceleration/deceleration. Furthermore, a smooth speed profile describes a gradual change in the speed of the AV 1604 to transition the AV 1604 from a first speed to a second speed. A smooth speed profile ensures that the AV 1604 transitions between speeds at a slower rate and therefore, reduces the force of acceleration/deceleration experienced by a passenger.

In an embodiment, the computer processors 1610 are configured to determine a steering profile. As described herein, steering profile represents the change in steering angle to orient the AV 1604 from a first direction to a second direction. For example, a jagged steering profile includes causing the AV 1604 to transition between orientations at higher/sharper angles. A jagged steering profile may cause passenger discomfort and may also lead to increased probability of the AV 1604 tipping over. A smooth steering profile includes causing the AV 1604 to transition between orientations at lower/wider angles. A smooth steering profile leads to increased passenger comfort and safety while operating the AV 1604 under varied environmental conditions.

In an embodiment, the computer processors 1610 are configured to determine a suspension setting for the AV 1604. This may include determining a suspension level (e.g., amount of lift) or a suspension stiffness. In an embodiment, the suspension level or suspension stiffness correlates with the load data. For example, higher suspension stiffness may indicate a heavier load and vice versa.

In an embodiment, the computer processors 1610 include one or more planning modules 1611. The planning modules 1611 may be substantially similar to the planning module 404 discussed previously with reference to FIG. 4. The planning modules may include a route planner, a speed profile planner, and/or a steering profile planner. The speed profile planner determines a desired speed profile for the AV 1604. The steering profile planner determines a desired steering profile for the AV 1604. In an embodiment, the computer processors 1610 are configured to update the planning modules 1611 based on the received load data 1651. In an embodiment, the planning modules 1611 provide information based on the load data 1651 that can be used to determine a heading for the AV 1604 and determine which road segments to traverse. In an embodiment, this information is used to generate the control commands 1612. In an embodiment, the computer processors 1610 are configured to assign weight values to the one or more load characteristics represented by the load data 1651.

The control systems 1620 are configured to receive and act on the control commands 1612 generated by the computer processors 1610. The control systems 1620 may comprise one control system or several control systems. In an embodiment, the control systems 1620 include control modules 1623. In an embodiment, the control modules 1623 are substantially similar to the control module 406 described previously with reference to FIG. 4. In an embodiment, control modules 1623 include controllers substantially similar to the controller 1102 described previously with reference to FIG. 11. However, the control systems 1620 may include various other types of controllers, such as door lock controllers, window controllers, turn-indicator controllers, windshield wiper controllers, suspension controllers and brake controllers.

The control systems 1620 also include control devices 1621. In an embodiment, the control devices 1621 facilitate the ability of the control systems 1620 to affect the control attributes 1640. As described herein a control attribute represents the various outputs associated with the control of the AV 1604. For example, a control attribute may relate to the speed of the AV 1604, the acceleration of the AV 1604, the deceleration of the AV 1604, the heading of the AV 1604, the height of the AV 1604, the tilt of the AV 1604, and so forth. Examples of control devices 1621 include, but are not limited to, a steering mechanism/column, wheels, axels, brake pedals, brakes, fuel systems, gear shifter, gears, throttle mechanisms (e.g., gas pedals), windshield wipers, side-door locks, window controls, suspension actuators and turn-indicators. In an embodiment, the control systems 1620 include a steering angle controller and a throttle controller. In an embodiment, the control systems 1620 affect the heading and/or throttle of the AV 1604 by directly controlling the wheels of the AV 1604. For example, the control systems 1620 may change the torque applied to one or more wheels of the AV 1604 to affect throttle operations. In an embodiment, the control systems 1620 affect the suspension level and/or suspension stiffness of the AV 1604. The control systems 1620 are configured to provide control output 1624 that affect one or more control attributes 1640 by, for example, modifying a value of a control attribute 1640. In an embodiment, the control attributes 1640 include an acceleration and the control output 1624 is data that is used for modifying the acceleration. In an embodiment, the control attributes 1640 include a steering angle and the control output 1624 is data used for modifying the steering angle. In an embodiment, the control attributes 1640 include a suspension setting and the control output 1624 is data that is used for modifying the suspension setting. In an embodiment, modifying the values of the control attributes 1640 include affecting the direction of motion (e.g., heading) of the AV 1604. In an embodiment, modifying a value of the control attributes 1640 includes changing the speed of the AV 1604. In an embodiment, the control systems 1640 modify the values of the control attributes 1640 by managing change in speeds and orientations of the AV 1604. This may include affecting the speed profile and/or steering profile of the AV 1604.

Figure 17:
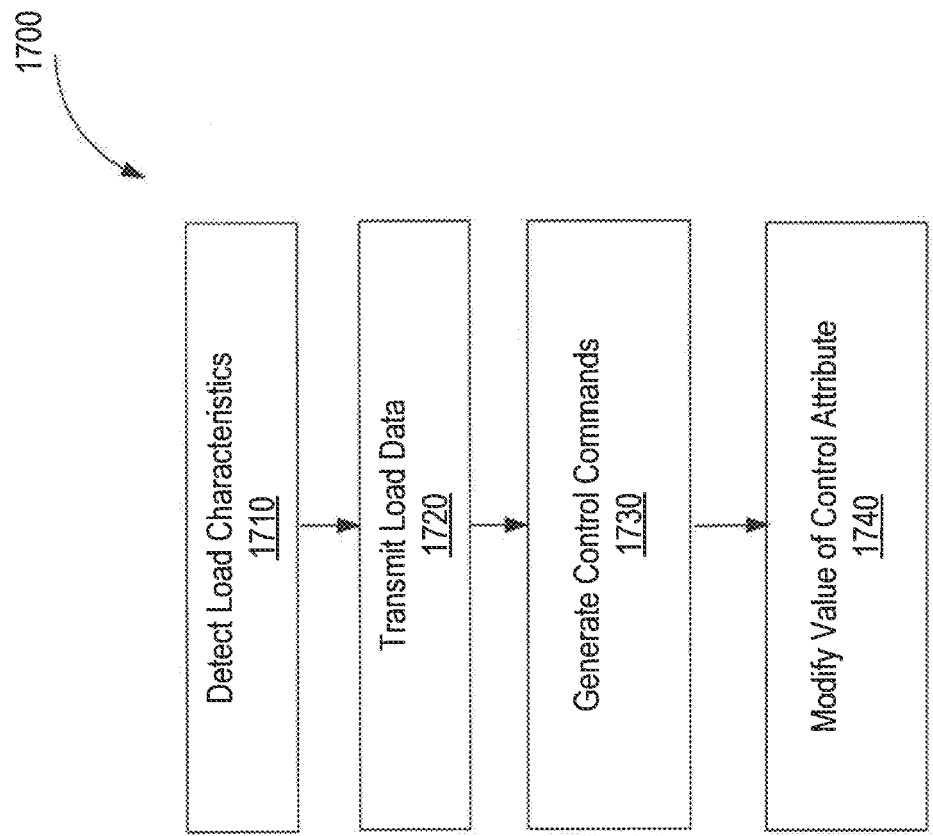
FIG. 17 illustrates a flowchart representing a method for controlling the output of actuators based on load characteristics, in accordance with one or more embodiments.

FIG. 17 illustrates a flowchart representing a method 1700 for controlling the output of actuators based on load characteristics according to at least one implementation of the present disclosure. In this illustrative example, the system 1600 for controlling actuators based on load characteristics described above with reference to FIG. 16 performs the method 1700 for controlling the output of actuators based on load characteristics. However this method can be performed by other systems involving devices for detecting load characteristics to control vehicles. The method 1700 includes detecting load characteristics (block 1710), transmitting load data (block 1720), generating control commands (block 1730), and modifying values of control attributes (block G340).

The method 1700 for controlling the output of actuators based on load characteristics includes detecting load characteristics (block 1710). The sensors 1650 detect one or more load characteristics of the AV 1604. For example, in an embodiment, the load sensors 1650 measure the weight of one or more passengers located within the AV 1604. In this instance, the sensors 1650 may include one or more load sensors located within or under the passenger seats of the AV 1604 to measure the weight of one or more passengers. In an embodiment, the sensors 1650 detect whether or not a seatbelt is being used and/or the strain applied to each seatbelt. Thus, the sensors 1650 may include one or more load sensors located within the seatbelt components of the passenger seats of the AV 1604. In an embodiment, the sensors 1650 measure the total weight of the AV 1604. Thus, the sensors 1650 may include one or more load sensors, inductive sensors, and/or capacitive sensors located on various locations of the AV's 1604 suspension system. Each of these sensors 1650 measure the total weight of the vehicle by detecting the displacement in certain components of the AV's 1604 suspension system. In an embodiment, the sensors 1650 include LiDARs, capacitive, and/or inductive sensors that measure the displacement/compression of the suspensions system's springs as passengers enter the AV 1604 and/or as cargo objects are placed within the AV 1604. In an embodiment, the sensors 1650 include load sensors to measure a force applied to the axles of the suspension system. In an embodiment, the sensors 1650 include cameras and/or LiDARs located within the AV's 1604 cabin to detect a number of passengers within the AV 1604, a number of cargo objects within the AV 1604, the build of one or more passengers aboard the AV 1604, the shape of one or more cargo objects within the AV 1604, or a combination thereof. In an embodiment, the sensors 1650 include one or more RFID readers (either active or passive) located within the cabin of the AV 1604 and configured to detect tags on one or more cargo objects. The tags may include information associated with the cargo objects' shape, size, fragility and/or weight.

In an embodiment, the AV 1604 is attached to a cargo vehicle (e.g., a towed vehicle, a trailer, etc.), using, for example, a hitch system. In an embodiment, one or more of the sensors 1650 are located on several locations of the hitch system, as discussed earlier, to measure the weight of the cargo vehicle or the tension resulting from pulling the cargo vehicle. In an embodiment, the sensors 1650 include one or more cameras and/or LiDARs located within the cabin of the cargo vehicle to detect the number of passengers within the cargo vehicle, a number of cargo objects within the cargo vehicle, the build of one or more passengers aboard the cargo vehicle, the shape of one or more cargo objects within the cargo, or a combination thereof. In an embodiment, the sensors 1650 include one or more RFID readers (either active or passive) located within the cabin of the AV 1604 and configured to detect tags on one or more cargo objects. The tags may include information associated with the cargo objects' shape, size, fragility, and/or weight.

In an embodiment, detecting load characteristics (block 1710) also includes receiving load data 1651 at the input devices 1670, the communications devices 1660, and/or the server 1630. The input devices 1670 are configured to receive load data 1651 from users of the AV 1604 representing one or more load characteristics. For example, users of the AV 1604 may input load data 1651 representing one or more load characteristics such as the age of one or more passengers, the weight of one or more passengers, health information (e.g., injury, illness, pregnancy status, etc.) of one or more passengers, a number of cargo object, the weight of one or more cargo objects, the shapes of one or more cargo objects, the position of one or more cargo objects, and/or the fragility of one or more cargo objects. In an embodiment, the communication devices 1660 receive load data 1651 from users of the AV 1604. In an embodiment, the server 1630 stores load data 1651 representing one or more load characteristics of the AV 1604, which is received from the communication devices 1660, other electronic devices, or other vehicles.

The method 1700 for controlling the output of actuators based on load characteristics includes transmitting load data (block 1720). The sensors 1650 transmit load data 1651 representing the detected load characteristics to the computer processors 1610. Because the load data 1651 represents the load characteristics, the load data 1651 carries information associated with: the weight of one or more passengers aboard the AV 1604; the weight of one or more passengers aboard a cargo vehicle attached to the AV 1604; the weight of one or more cargo objects in the AV 1604; the weight of one or more cargo objects in a cargo vehicle attached to the AV 1604; the location of one or more passengers aboard the AV 1604; the location of one or more passengers aboard a cargo vehicle attached to the AV 1604; the location of one or more objects within the AV 1604; the location of one or more objects within a cargo vehicle attached to the AV 1604; the shape/build of one or more passengers aboard the AV 1604; the shape/build of one or more passengers aboard a cargo vehicle attached to the AV 1604; the shape/build of one or more cargo objects within the AV 1604; the shape/build of one or more cargo objects within a cargo vehicle attached to the AV 1604; characteristics associated with seatbelt usage information; the weight of the AV 1604; the weight of a cargo vehicle attached to the AV 1604; the age of one or more passengers of the AV 1604, characteristics associated with health information of the AV 1604 or a combination thereof.

The method 1700 for controlling the output of actuators based on load characteristics includes generating control commands (block 1730). The computer processors 1610 generate control commands 1612 based on the received load data 1651. In an embodiment, the control commands 1612 reflect one or more determinations made by the computer processors 1610. For example, in an embodiment, the computer processors 1610 determine the acceleration required for the AV 1604 to reach or maintain a predetermined speed based at least partially on the vehicle/passenger/object weight information within the load data 1651. In an embodiment, as the load weight of the AV 1604 increases, the computer processors 1610 determine an increasing rate of acceleration is needed to reach or maintain a predetermined speed. The computer processors 1610 may also determine that the AV 1604 should travel at reduced speeds as the load weight increases because it may take longer to decelerate under such conditions. In an embodiment, as the weight of the load decreases, the computer processors AV 1604 determine that less throttle is needed to reach or maintain a predetermined speed. The computer processors may determine that the AV 1604 can travel at higher speeds as the weight of the load decreases because the AV 1604 may be more responsive to deceleration controls (e.g., braking) under such conditions. Similarly, as the load weight increases, the computer processors 1610 may determine that more deceleration (e.g., more braking) is needed to reach or maintain a predetermined speed. As the load weight decreases, the computer processors 1610 may determine that less deceleration is needed to reach or maintain a predetermined speed.

In an embodiment, the computer processors 1610 determine a desired speed profile based on the load data 1651. As indicated previously with reference to FIG. 16, speed profile relates to the change in acceleration or jerk to cause the AV 1604 to transition from a first speed to at least a second speed. As the load weight decreases, the computer processors 1610 may determine that a smoother speed profile is desired because the lighter weight of the AV 1604 does not allow for higher changes in acceleration or jerk. Similarly, if the load data 1651 indicates that a cargo vehicle attached to the AV 1604 contains a heavy load, the computer processors 1610 may determine that a smoother speed profile is desired. Furthermore, if the load data 1651 indicates that one or more cargo objects inside the AV 1604 (or an attached cargo vehicle) are fragile, the computer processors 1610 may determine that a smoother speed profile is desired to prevent the objects from becoming damaged.

In an embodiment, the computer processors 1610 determine a steering profile based on the vehicle/passenger/object weight. As indicated previously with reference to FIG. 16, steering profile relates to the change in steering angle to orient the AV 1604 from a first direction to a second direction. In an embodiment, as the load weight increases, the computer processors 1610 determine that a smoother steering profile is desired. This, for example, may decrease the likelihood of the AV 1604 tipping over while making turns when the AV 1604 is operating under heavy conditions. As the load weight decreases, the computer processors 1610 may determine that a more jagged steering profile is desired. In an embodiment, the computer processors 1610 use load data 1651 information associated with object location, passenger location, object shape, passenger build, and/or seatbelt usage to determine how much to affect the steering angle to steer the vehicle in a desired direction. For example, the computer processors 1610 may use some or all of the aforementioned information to determine a center of mass for the AV 1604, and then based on the determined center of mass, determine a steering profile. If the load data 1651 indicates that one or more passengers are not wearing a seatbelt, the computer processors 1610 may determine that a smoother steering profile is desired for passenger safety reasons. Moreover, if the load data 1651 indicates that one or more cargo objects within the AV 1604 (or an attached cargo vehicle) are fragile, the computer processors 1610 may determine that that a smoother steering profile is desired to prevent the cargo objects from being damaged.

In an embodiment, the computer processors 1610 are configured to determine a suspension setting for the AV 1604 based on the load data 1651. For example, if the load data 1651 indicates that the AV 1604 is operating under conditions causing its suspension system to become compressed, the computer processors 1610 may determine that the level (i.e. lift) of the AV's 1604 suspension system should be increased. The computer processors may also determine that the AV's 1604 suspension system should have less stiffness when, for example, the AV 1604 contains fragile cargo objects that may require a smoother, less bumpy transport.

As indicated earlier, in an embodiment, the computer processors 1610 include a planning modules 1611. In an embodiment, the planning modules 1611 include a route planner that receives data representing a destination and determines data representing a trajectory (sometimes referred to as a route) that can be traveled by the AV 1604 to reach (e.g., arrive at) a destination. Generally, in order for the planning modules 1611 to determine the data representing the trajectory, the planning modules 1611 receive data from a perception module, a localization module, and a database module, such as the perception module 402, the localization module 408, and the database module 410 described earlier with reference to FIG. 4. In an embodiment, the planning modules 1611 also receive the load data 1651, and use the load data 1651 to determine the data representing a desired trajectory.

For example, the load data 1651 may indicate that the AV 1604 is operating under heavy conditions, one or more passengers are not wearing a seatbelt, and/or one or more objects are fragile. In this instance, the planning module 1611 may determine that a trajectory which includes flatter, straighter, and less bumpy roads is desirable. In an embodiment, the planning modules 1611 include a speed profile planner that can determine a desired speed profile for the AV 1604 based on the load data 1651 and optionally the determined trajectory. For example, the speed profile planner can determine when the AV 1604 should begin accelerating along a road segment based on the load weight of the AV 1604. In an embodiment, as the load weight increases, the speed profile planner determines that a smoother speed profile is desired, which may require a longer acceleration period.

In an embodiment, the planning modules 1611 include a steering profile planner that can determine a desired steering profile for the AV 1604 based on the load data 1651 and optionally the determined trajectory. For example, as the load weight increases, the steering profile planner may determine that a smoother steering profile is desired, which may require initiating steering angle controls at an earlier point in a road segment.

In an embodiment, the planning modules 1611 include a suspension setting planner that can determine a desired suspension setting for the AV 1604 based on the load data 1651 and optionally the determined trajectory. For example, if the AV 1604 comprises one or more pregnant passengers, and/or the AV 1604 will be traversing along a bumpy road, the suspension setting planner can determine that the stiffness setting of the suspension system should be decreased, allowing for a less bumpy transport. As another example, if the AV 1604 is operating under heavy conditions causing the suspension system to become compressed, suspension setting planner can identify road segments that may require the height of the vehicle to increase, and determine to increase the suspension lift at those identified road segments. In an embodiment the computer processors 1610 generate control commands 1612 reflecting, at least partially, the determinations made by the planning modules 404.

In an embodiment, the computer processors 1610 assign a weighting value to each of the one or more load characteristics represented by the load data 1651 to generate the control commands 1612. For example, in an embodiment, the computer processors 1610 assign a higher weight value to load data 1651 indicating a fragile object than load data 1651 indicating the total weight of the AV 1604. Consequently, the computer processors 1610 may determine that a smooth steering and/or speed profile is desired, even as the load weight decreases, when fragile objects are placed inside the AV 1604 or an attached cargo vehicle. In an embodiment, the computer processors 1610 assign a higher weight value to load data 1651 indicating that one or more passengers are not wearing a seatbelt, and thus the computer processors 1610 may determine that a smoother steering and/or speed profile is desired, even as the load weight decreases, when passengers are not wearing seatbelts. The computer processors 1610 may also assign a higher weight value to load data 1651 associated with a cargo vehicle attached to the AV 1604 than the AV 1604 itself because the cargo vehicle may have an increased sensitivity to tipping during turns.

The method 1700 also includes modifying values of control attributes (block 1740). In response to receiving control commands 1612, the control systems 1620 provide a control output 1624 that affects at least one of the control attributes 1640. The control output 1624 can be data useable for acceleration control and/or data useable for steering angle control. The control output 1624 can be data useable for suspension setting control. The control output 1624 can include control algorithms. For example, the algorithms can be feedback algorithms based on feedback received from feedback systems as described earlier with reference to FIG. 11.

For example, if the control commands 1612 indicate that the AV 1604 needs to accelerate by an amount (x), the control systems 1620 can cause the AV 1604 to accelerate by affecting a throttle mechanism or by directly controlling the amount of torque applied directly to each of the wheels of the AV 1604. If the control commands 1612 indicate that the AV 1604 needs to change its heading by an amount (y), the control systems 1620 can cause the AV 1604 to change its heading by affecting a steering column or directly controlling the orientation of the AV's 1604 wheels.

The control output 1624 is generated in accordance with at least one input. In an embodiment, the input may be the control commands 1612 that provide information used by the control systems 1624 to choose a heading for the AV 1604 and determine which road segments to traverse. The input may also correspond to information received from a localization module, which provides information describing the AV's 1604 current location so that the control system 1620 can determine if the AV 1604 is at a location expected based on the manner in which the AV's 1604 devices are being controlled. The input may also correspond to feedback modules, as described earlier with reference to FIG. 11. The input may also include information received from databases, computer networks, etc. In an embodiment, the input is a desired output. The desired output may include speed and heading based on the information received by, for example, the planning module 1611.

Figure 18:
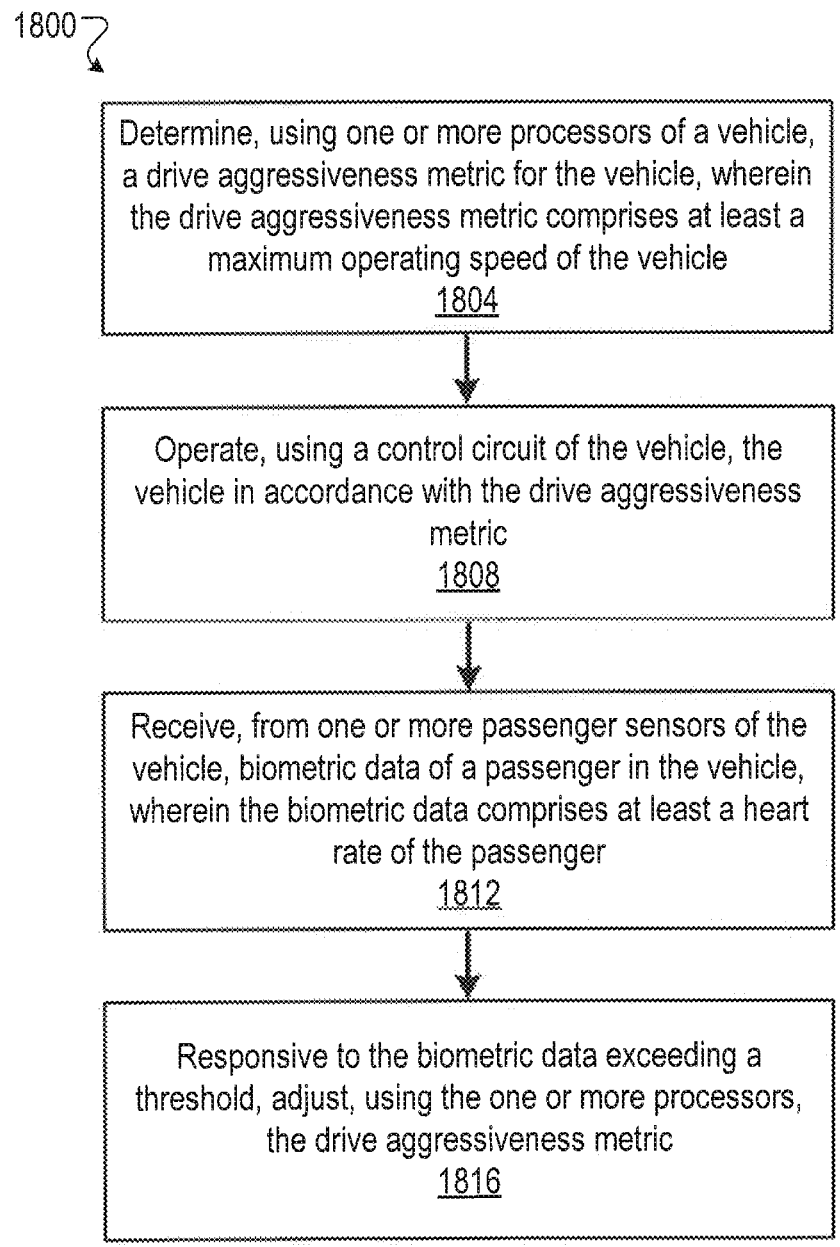
FIG. 18 illustrates a process for measuring and increasing passenger comfort during the operation of a vehicle, in accordance with one or more embodiments.

FIG. 18 illustrates a process 1800 for measuring and increasing passenger comfort during the operation of the AV 1304, in accordance with one or more embodiments. In one embodiment, the process 1800 of FIG. 18 is performed by one or more components (e.g., the planning module 1328 in FIG. 13) of the AV 1304. Other entities (e.g., a remote server 1312 in FIG. 13) perform some or all of the steps of the process 1800 in other embodiments. Likewise, embodiments may include different and/or additional steps, or perform the steps in different orders.

The AV 1304 determines 1804, using one or more processors 146, a drive aggressiveness metric for the AV 1304. The drive aggressiveness metric includes at least a maximum operating speed of the AV 1304. A drive aggressiveness metric is an aggregate value (e.g., weighted average) of the parameters (e.g., maximum speed, maximum acceleration, etc.,) in a vehicle operation profile. The drive aggressiveness metric represents a degree of aggressiveness in driving.

The AV 1304 operates 1808, using a control module 1336, the AV 1304 in accordance with the drive aggressiveness metric. The control module 1336 receives data representing the drive aggressiveness metric and data representing the AV 1304 position and operates the control functions 420a-c (e.g., steering, throttling, braking, ignition) of the AV 1304 in a manner that will cause the AV 1304 to travel a trajectory to a destination.

The AV 1304 receives 1812, from one or more passenger sensors 1348 of the AV 1304, biometric data of a passenger in the AV 1304. The biometric data includes at least a heart rate of the passenger. The biometric data for each passenger includes biofeedback measurements and values derived from such measurements. In one example, the biometric data includes the passenger's skin conductance, pulse, heart-rate, body temperature, facial expressions, magnitude of pupil dilation, or pressure exerted by the passenger on seat arm rests.

Responsive to the biometric data exceeding a threshold, the AV 1304 adjusts 1816, using the one or more processors 146, the drive aggressiveness metric. For example, for multiple passengers in the AV 1304, the AV 1304 may tune the performance based on calculating an average of various passenger comfort characteristics based on a user profile of each passenger. The one or more processors 146 is used to adjust the drive aggressiveness metric based on the aggregate passenger comfort metric.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A method comprising:
    determining, using one or more processors, a vehicle operation profile for an autonomous vehicle, the determining of the vehicle operation profile comprising aggregating a plurality of stored passenger profiles, the plurality of stored passenger profiles matching demographic data of a stored passenger profile of at least one passenger located within the autonomous vehicle;
    measuring, using the one or more processors, passenger data detected by sensors of the autonomous vehicle, the passenger data corresponding to the at least one passenger;
    updating, using the one or more processors with a machine learning model, the vehicle operation profile based on the passenger data, wherein the passenger data comprises a weighted aggregate of passenger comfort data of the at least one passenger in the autonomous vehicle; and
    controlling, using the one or more processors, actuators of the autonomous vehicle using the updated vehicle operation profile.

2. The method of claim 1, wherein the passenger data comprises biometric data of the at least one passenger.

3. The method of claim 1, wherein the vehicle operation profile is partially determined based on data received from the stored passenger profile of the at least one passenger.

4. The method of claim 1, wherein the stored passenger profile of the at least one passenger comprises biometric data of the at least one passenger recorded on previous vehicle rides.

5. The method of claim 1, wherein the stored passenger profile of the at least one passenger comprises demographic data of the at least one passenger recorded on previous vehicle rides or obtained from the at least one passenger.

6. The method of claim 1, wherein the stored passenger profile of the at least one passenger comprises personal preference data of the at least one passenger recorded on previous vehicle rides or obtained from the at least one passenger.

7. The method of claim 1, wherein the sensors comprise one or more biometric sensors and the passenger data comprises at least one of a skin conductance, a pulse, a heart-rate, or a body temperature.

8. The method of claim 1, wherein the sensors comprise one or more imaging sensors and the passenger data comprises at least one of facial expressions or a magnitude of pupil dilation.

9. The method of claim 1, wherein the sensors comprise one or more pressure sensors and the passenger data comprises a pressure exerted by the at least one passenger on seat arm rests.

10. The method of claim 1, wherein the passenger data is associated with at least one of a time of day, a geographical location, a pattern of traffic, or a weather pattern.

11. The method of claim 1, wherein the sensors comprise at least one of a heart rate monitor, a sphygmomanometer, a pupilometer, an infrared thermometer, or a galvanic skin response sensor.

12. The method of claim 1, wherein the vehicle operation profile comprises at least one of a maximum speed limit, a maximum longitudinal acceleration limit, a maximum amplitude of fluctuation of acceleration, a maximum lateral acceleration, a maximum change in steering angle, a maximum rate of turn, or a maximum limit on a magnitude of jerk of the autonomous vehicle.

13. The method of claim 1, wherein the vehicle operation profile comprises at least one of a lateral clearance of the autonomous vehicle from an object or a lateral clearance of the autonomous vehicle from a pedestrian located in an environment containing the autonomous vehicle.

14. The method of claim 1, wherein the vehicle operation profile is determined based on data received, using an input device of the autonomous vehicle, from the at least one passenger.

15. The method of claim 1, wherein the passenger data is measured at different operating speeds of the autonomous vehicle.

16. The method of claim 1, further comprising adjusting a trajectory of the autonomous vehicle based on at least one of the passenger data or data received from a stored passenger profile of the at least one passenger.

17. The method of claim 1, further comprising transmitting, using a display of the autonomous vehicle, data representing ride pricing incentives to the at least one passenger to incentivize the at least one passenger to allow biometric data collection within the autonomous vehicle.

18. An autonomous vehicle comprising:
    one or more computer processors; and
    one or more non-transitory storage media storing instructions which, when executed by the one or more computer processors, cause the one or more computer processors to:
        determine a vehicle operation profile for the autonomous vehicle, the determining of the vehicle operation profile comprising aggregating a plurality of stored passenger profiles, the plurality of stored passenger profiles matching demographic data of a stored passenger profile of at least one passenger located within the autonomous vehicle;

measure passenger data detected by sensors of the autonomous vehicle, the passenger data corresponding to the at least one passenger;

update the vehicle operation profile with a machine learning model based on the passenger data, wherein the passenger data comprises a weighted aggregate of passenger comfort data of the at least one passenger in the autonomous vehicle; and control one or more actuators of the autonomous vehicle using the updated vehicle operation profile.

19. A non-transitory storage medium storing instructions which, when executed by one or more computing devices, cause the one or more computing devices to:

determine a vehicle operation profile for an autonomous vehicle, the determining of the vehicle operation profile comprising aggregating a plurality of stored passenger profiles, the plurality of stored passenger profiles matching demographic data of a stored passenger profile of at least one passenger located within the autonomous vehicle;

measure passenger data detected by sensors of the autonomous vehicle, the passenger data corresponding to the at least one passenger;

update the vehicle operation profile with a machine learning model based on the passenger data, wherein the passenger data comprises a weighted aggregate of passenger comfort data of the at least one passenger in the autonomous vehicle; and control one or more actuators of the vehicle using the updated vehicle operation profile.

20. The one or marc non-transitory storage medium of claim 19, wherein the passenger data comprises biometric data of the at least one passenger.

* * * * *

UNITED STATES PATENT AND TRADEMARK OFFICE
CERTIFICATE OF CORRECTION

PATENT NO. : 11,648,951 B2  
APPLICATION NO. : 16/656655  
DATED : May 16, 2023  
INVENTOR(S) : Scott D. Pendleton and Maurilio Di Cicco Page 1 of 1

It is certified that error appears in the above-identified patent and that said Letters Patent is hereby corrected as shown below:

On the Title Page

Item (12), should read Pendleton.

Column 1, Item (72), delete "Pendelton," and insert -- Pendleton, -- therefor.

In the Claims

Column 46, Line 14, In Claim 20, after "The" delete "one or marc".

Signed and Sealed this  
First Day of August, 2023

*Katherine Kelly Vidal*

Katherine Kelly Vidal  
*Director of the United States Patent and Trademark Office*